(12) United States Patent
McArthur et al.

(10) Patent No.: US 9,265,877 B2
(45) Date of Patent: Feb. 23, 2016

(54) DEVICES, SYSTEMS AND METHODS FOR CARBON DIOXIDE ANGIOGRAPHY

(71) Applicant: Merit Medical Systems, Inc., South Jordan, UT (US)

(72) Inventors: Gregory R. McArthur, Sandy, UT (US); Brian Stevens, Pleasant Grove, UT (US); William Padilla, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 410 days.

(21) Appl. No.: 13/756,798

(22) Filed: Feb. 1, 2013

(65) Prior Publication Data

US 2013/0204130 A1 Aug. 8, 2013

Related U.S. Application Data

(60) Provisional application No. 61/594,740, filed on Feb. 3, 2012.

(51) Int. Cl.
| | |
|---|---|
| *A61M 5/00* | (2006.01) |
| *A61M 5/178* | (2006.01) |
| *A61M 5/31* | (2006.01) |
| *A61M 39/22* | (2006.01) |
| *A61B 6/00* | (2006.01) |
| *A61M 5/315* | (2006.01) |

(52) U.S. Cl.
CPC .............. *A61M 5/007* (2013.01); *A61M 5/178* (2013.01); *A61M 5/1782* (2013.01); *A61B 6/481* (2013.01); *A61B 6/504* (2013.01); *A61M 5/3134* (2013.01); *A61M 5/3137* (2013.01); *A61M 5/31551* (2013.01); *A61M 5/31555* (2013.01); *A61M 2005/3114* (2013.01); *A61M 2039/224* (2013.01); *A61M 2202/0225* (2013.01)

(58) Field of Classification Search
CPC ................... A61M 2005/1402; A61M 39/223; A61M 5/14216; A61M 5/36; A61M 5/00; A61M 2039/224; A61M 5/007; A61M 2005/006; A61M 2202/0225; A61M 2005/3114; A61M 5/1782; A61M 5/3134; F16K 11/0716; A61B 6/481
See application file for complete search history.

(56) References Cited

U.S. PATENT DOCUMENTS

| | | | | |
|---|---|---|---|---|
| 3,752,145 | A * | 8/1973 | Runnells et al. | 600/432 |
| 5,249,579 | A * | 10/1993 | Hobbs et al. | 600/458 |
| 5,603,700 | A * | 2/1997 | Daneshvar | 604/122 |
| 2009/0093734 | A1 * | 4/2009 | Stevenson | 600/560 |

OTHER PUBLICATIONS

Optimized Global Care, CO2-Angioset brochure, Http://www.opti-med.de/nc/en/products/category/vascular-interventions/product-details/p-kategorie/vaskulaere-interventionen/subkategorie/co2-angioset/p-produkt/co2-angioset-nach-schmitz-rodealzen. Accessed Nov. 19, 2013.

* cited by examiner

*Primary Examiner* — Theodore Stigell
*Assistant Examiner* — Benjamin Koo
(74) *Attorney, Agent, or Firm* — Stoel Rives LLP

(57) ABSTRACT

Disclosed herein are various embodiments of devices, systems and methods for the delivery of carbon dioxide ($CO_2$) as a contrast agent for angiography. The $CO_2$ delivery device can include a syringe and a shuttle valve assembly in fluid communication with the syringe, such that the shuttle valve can be disposed in a first position to pressurize the syringe with $CO_2$, and a second position to deliver a bolus of $CO_2$ to a subject.

21 Claims, 18 Drawing Sheets

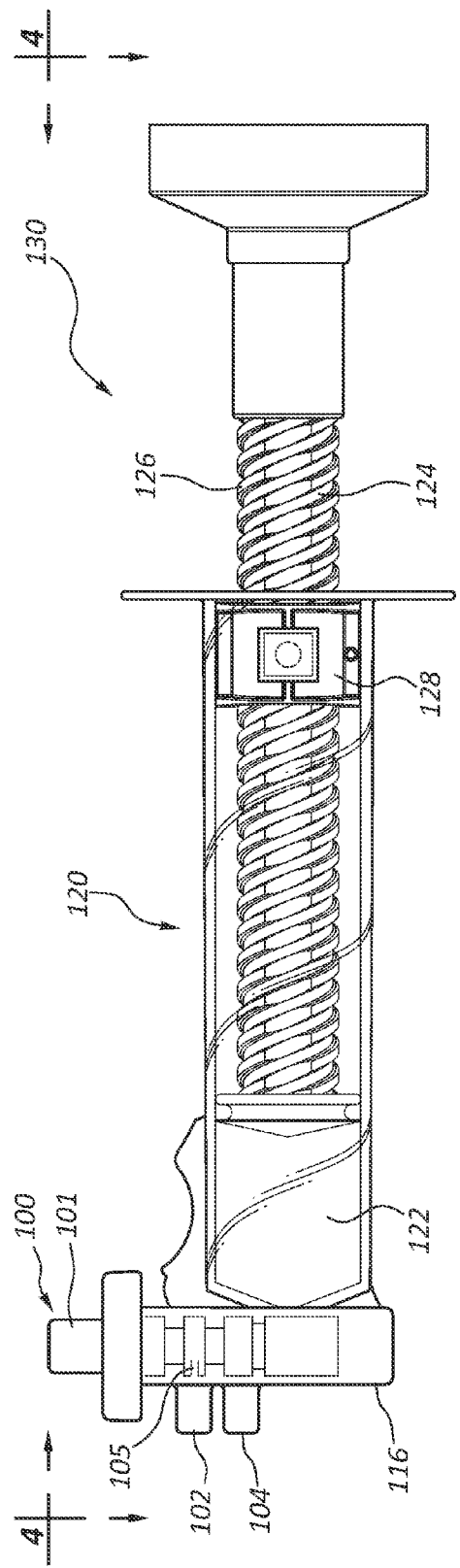
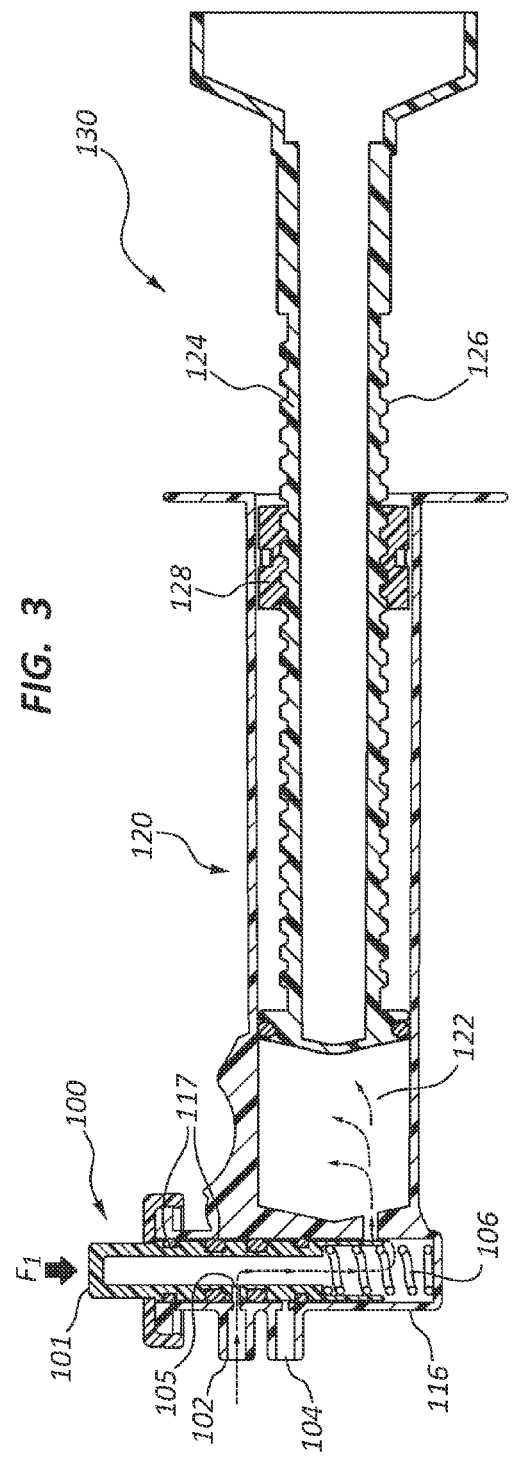
FIG. 3
FIG. 4

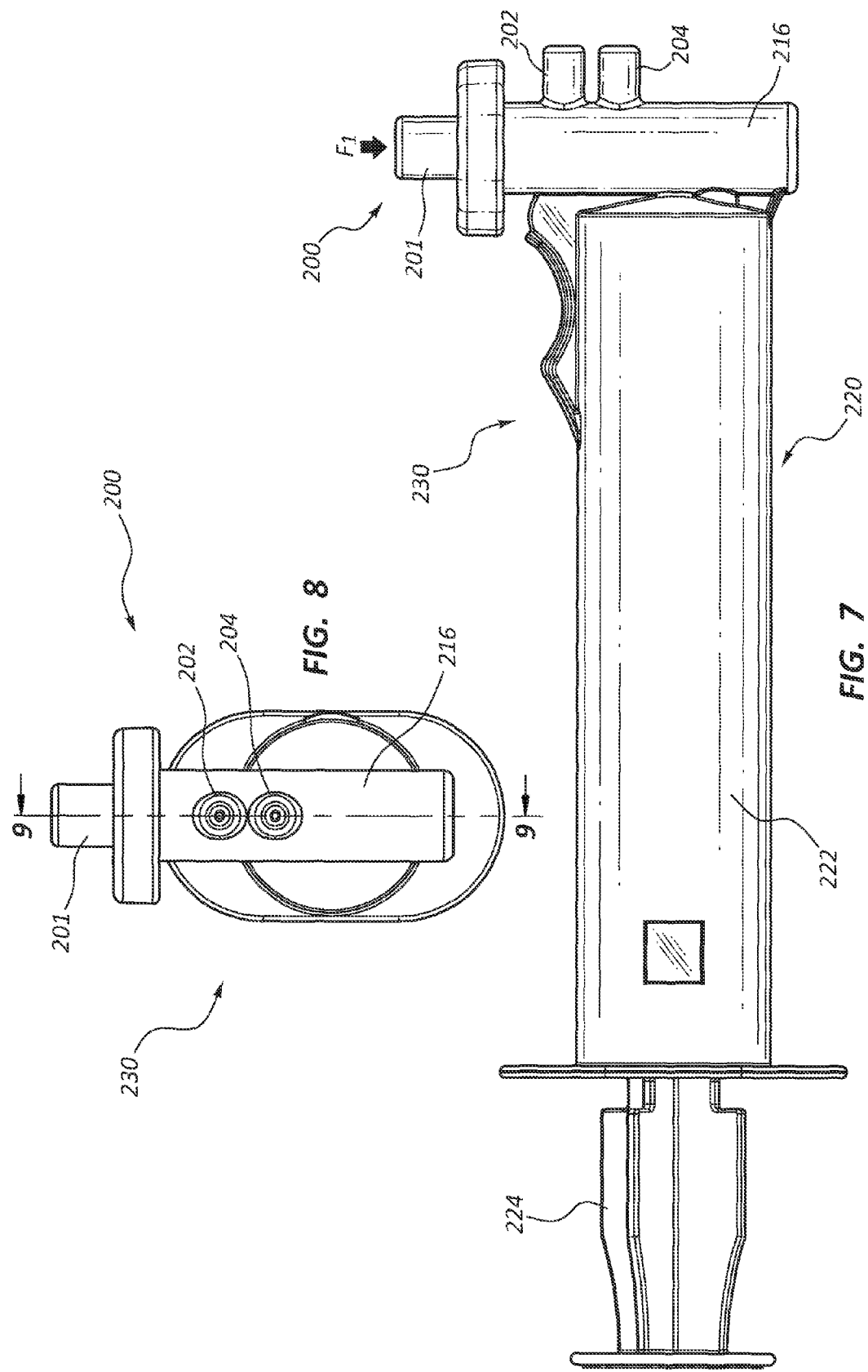

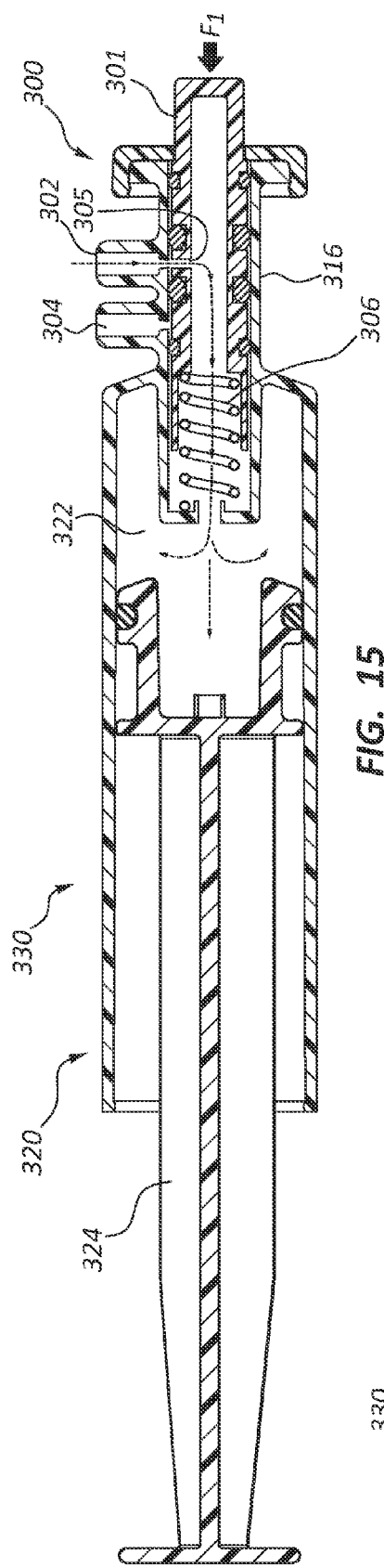
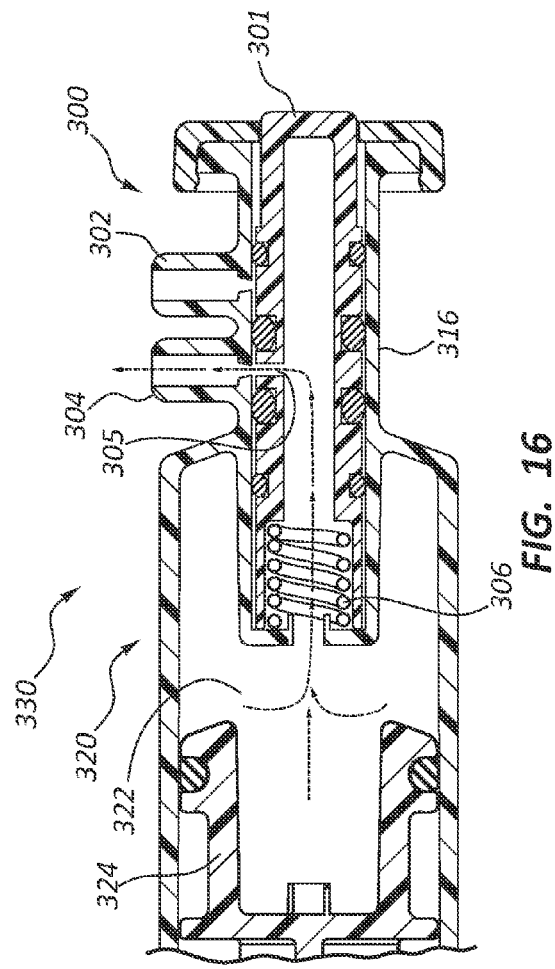
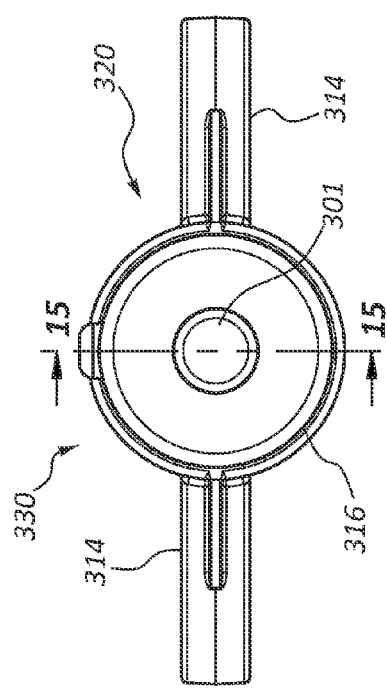
FIG. 15
FIG. 16
FIG. 14

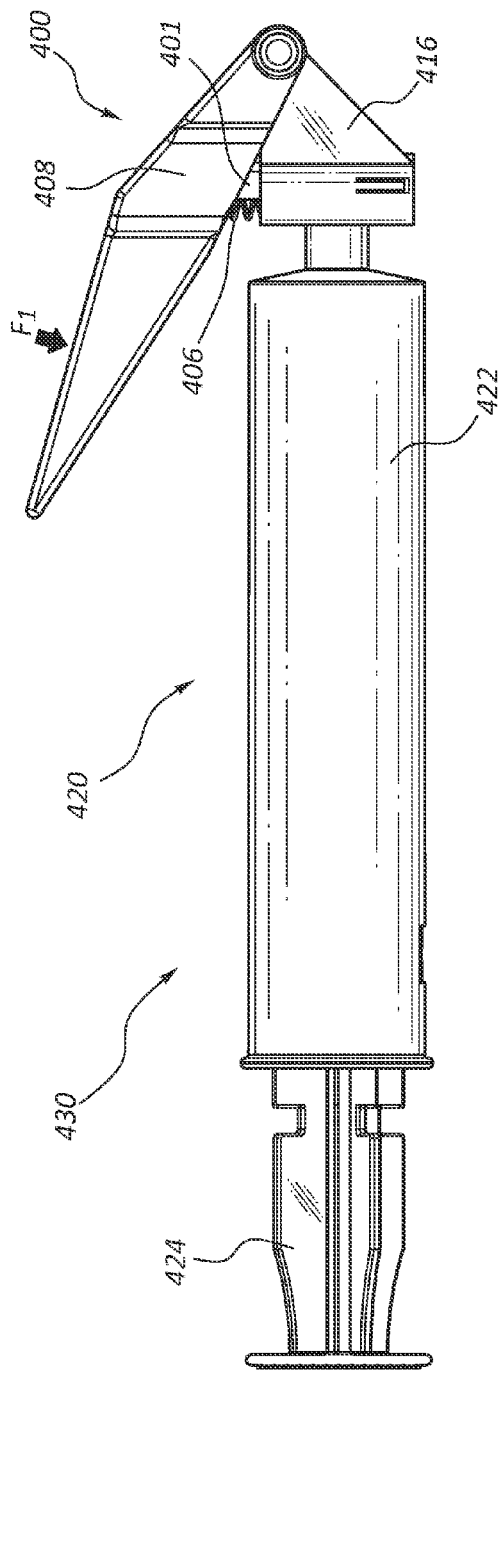
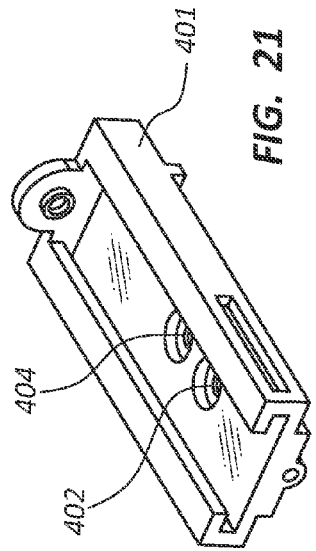
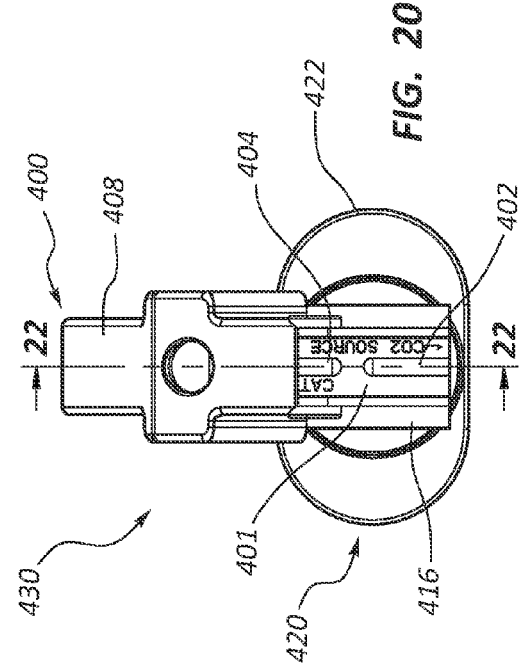

DEVICES, SYSTEMS AND METHODS FOR CARBON DIOXIDE ANGIOGRAPHY

RELATED APPLICATIONS

This application claims priority to U.S. Provisional Application No. 61/594,740 filed on Feb. 3, 2012, titled "Devices, Systems and Methods for Carbon Dioxide Angiography," which is hereby incorporated by reference in its entirety.

TECHNICAL FIELD

The present disclosure relates generally to medical devices. In particular, the present disclosure relates to devices, systems and methods for vascular interventions using carbon dioxide ($CO_2$) as a contrast agent. Certain embodiments relate, more particularly, to devices, systems and methods for delivering $CO_2$ to a subject for use as a contrast agent for angiography.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 3 is a side view of the $CO_2$ delivery device 130 of FIG. 2.

FIG. 4 is a cross sectional view of the $CO_2$ delivery device 130 of FIG. 3. This cross sectional view illustrates the $CO_2$ delivery device 130 in a first position, such that the chamber 122 of the syringe 120 is in fluid communication with the first port 102 of the shuttle valve assembly 100.

FIG. 7 is a side view of the $CO_2$ delivery device 230 of FIG. 6.

FIG. 8 is a front view of one end of the $CO_2$ delivery device 230 illustrated in FIG. 6.

FIG. 14 is a front view of one end of the $CO_2$ delivery device 330 illustrated in FIG. 11.

FIG. 15 is a cross sectional view of the $CO_2$ delivery device 330 of FIG. 13. This cross sectional view illustrates the $CO_2$ delivery device 330 in a first position, such that the chamber 322 of the syringe 320 is in fluid communication with the first port 302 of the shuttle valve assembly 300.

FIG. 16 is an enlarged, partially cut away cross sectional view of a shuttle valve assembly 300 connected to a syringe 320. This enlarged cross sectional view illustrates the $CO_2$ delivery device 330 in a second position, such that the chamber 322 of the syringe 320 is in fluid communication with the second port 304 of the shuttle valve assembly 300.

FIG. 19 is a side view of the $CO_2$ delivery device 430 of FIG. 17.

FIG. 20 is a top view of one end of the $CO_2$ delivery device 430 illustrated in FIG. 17.

FIG. 21 is a bottom perspective view of the valve block 401 of the shuttle valve assembly 400.

DETAILED DESCRIPTION

Figure 1:
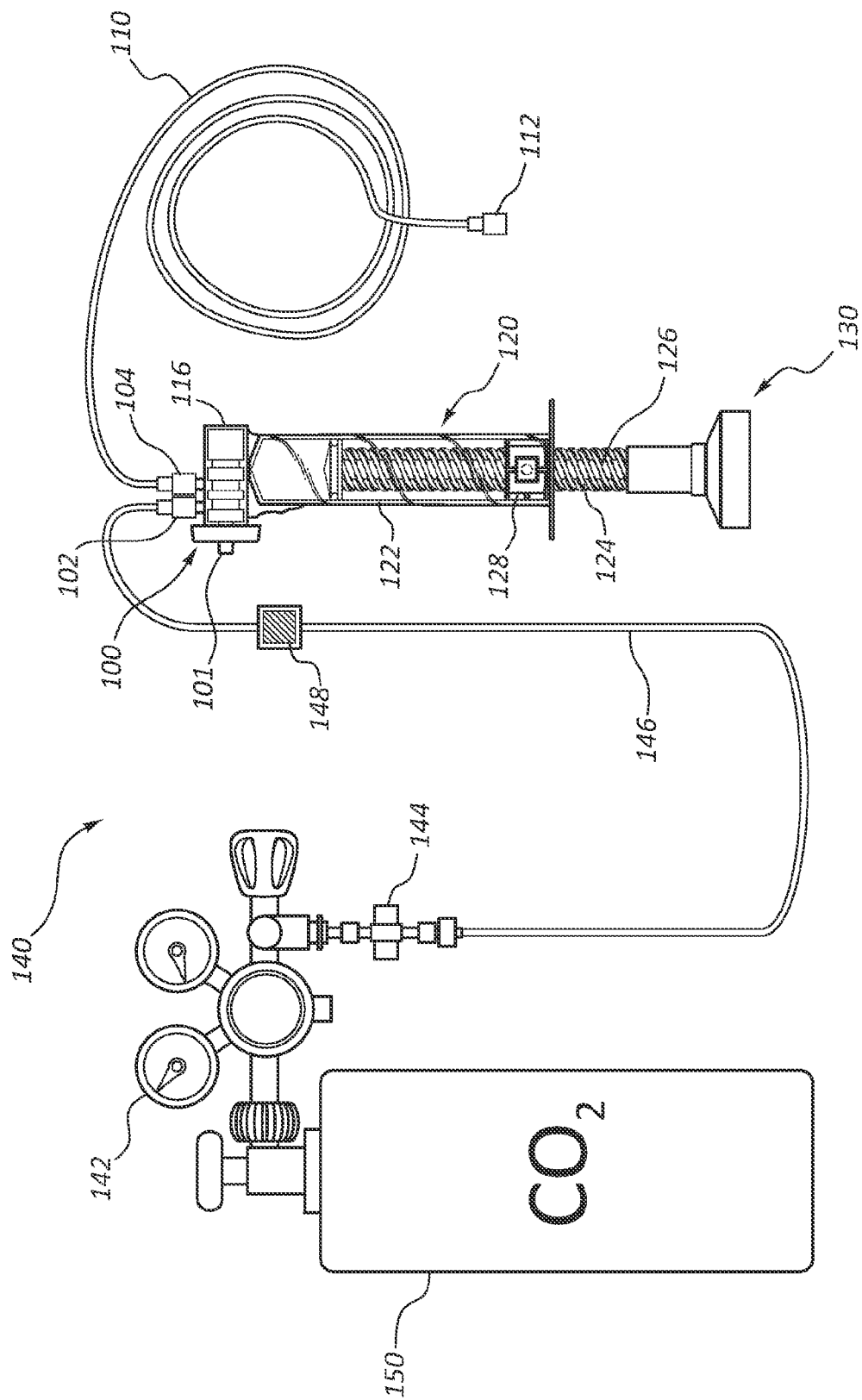
FIG. 1 is a schematic diagram of an exemplary carbon dioxide ($CO_2$) angiography system, illustrating a $CO_2$ supply assembly 140, $CO_2$ delivery device 130 and a connection line 110.

Traditionally, iodinated contrast agents (e.g., iohexol, iodixanol and iopromide) have typically been used for angiography. While iodinated contrast agents are generally harmless to most subjects, side effects, including anaphylactic reactions and contrast-induced nephropathy that are associated with such contrast agents, still exist. Additionally, iodinated contrast agents may not be suitable for use in certain subjects who are hypersensitive to iodinated contrast agents or whose renal function is compromised. The use of $CO_2$ as an angiographic contrast agent has increased because of its cost-effectiveness relative to traditional contrast agents, and its use has not been found to be associated with allergic reactions or nephrotoxicity. As will be appreciated, $CO_2$ may not be suitable for use as an arterial contrast agent above the diaphragm due to the risk of gas embolism of the coronary, cerebral and spinal arteries. However, $CO_2$ may be used as a contrast agent in sites below the diaphragm or in the extremities for various types of angiography, including cholangiography, nephrography, gastrography and the like.

Devices, systems and methods for angiography using carbon dioxide ($CO_2$) as a contrast agent are described herein. The methods, systems and devices disclosed are suited for delivering $CO_2$ to a subject for use as an angiographic contrast agent. The methods described herein include using a $CO_2$ delivery device to deliver $CO_2$ as an angiographic contrast agent. The devices described herein include $CO_2$ delivery devices that are configured for one-handed operation and increased adjustability of the volume of $CO_2$ to be delivered to a subject.

For example, in certain embodiments, the $CO_2$ delivery device may include a shuttle valve assembly having a valve base that receives a valve block. In such an embodiment, a biasing member may be disposed between the valve block having an opening, and the valve base having a first port and a second port. The shuttle valve assembly may include one or more sealing members disposed between the valve block and the valve base. The shuttle valve assembly may be connected to a syringe having a chamber and a plunger.

When no force is applied to the valve block against the biasing member, the $CO_2$ delivery device maintains a first position, wherein the opening of the valve block is substantially aligned with the first port of the valve base, while the second port of the valve base is isolated between two sealing members. The first position allows the first port of the shuttle valve assembly to be in fluid communication with the chamber of the syringe, while the second port is isolated and/or closed from being in fluid communication with the chamber of the syringe. In one embodiment, the first port may be connected to at least one $CO_2$ source, such that the $CO_2$ source is in fluid communication with the chamber of the syringe. In such an embodiment, $CO_2$ may flow from the $CO_2$ source to fill the chamber of the syringe when the $CO_2$ delivery device is maintained in the first position.

When a force is applied to the valve block against the biasing member, the $CO_2$ delivery device engages in a second position. In the second position, the opening of the valve block is substantially aligned with the second port of the valve base. When engaged in the second position, the chamber of the syringe is in fluid communication with the second port of the shuttle valve assembly, while the first port is isolated and/or closed from being in fluid communication with the chamber of the syringe. In one embodiment, the second port may be connected to or otherwise in fluid communication with a connection line suitable for delivering $CO_2$ to a subject. In such an embodiment, $CO_2$ may be delivered to the subject from the chamber of the syringe when the $CO_2$ delivery device is engaged in the second position.

In alternative embodiments, the $CO_2$ delivery device may include a shuttle valve assembly having a valve base that receives a valve block. In such an embodiment, a biasing member may be disposed between the valve block having a first port and a second port, and the valve base having an opening. The shuttle valve assembly may be connected to a syringe having a chamber and a plunger.

When no force is applied to the valve block against the biasing member, the $CO_2$ delivery device maintains a first position, wherein the opening of the valve base is substantially aligned with the first port of the valve block. The first position allows the chamber of the syringe to be in fluid communication with the first port of the shuttle valve assembly, while the second port is isolated and/or closed from being in fluid communication with the chamber of the syringe. In one embodiment, the first port may be connected to at least one $CO_2$ source, such that the $CO_2$ source is in fluid communication with the chamber of the syringe. In such an embodiment, $CO_2$ may flow from the $CO_2$ source to fill the chamber of the syringe when the $CO_2$ delivery device is maintained in the first position.

When a force is applied to the valve block against the biasing member, the $CO_2$ delivery device engages in a second position. In the second position, the opening of the valve base is substantially aligned with the second port of the valve block. When engaged in the second position, the chamber of the syringe is in fluid communication with the second port, while the first port is isolated and/or closed from being in fluid communication with the chamber of the syringe. In one embodiment, the second port may be connected to or otherwise in fluid communication with a connection line suitable for delivering $CO_2$ to a subject. In such an embodiment, $CO_2$ may be delivered to the subject from the chamber of the syringe when the $CO_2$ delivery device is engaged in the second position.

As will be appreciated, the configuration of the $CO_2$ delivery device may be reversed, such that the first position is engaged when a force is applied to the actuating member and/or valve block against the biasing member, and the second position is engaged when the force is released. In one embodiment, to load the syringe chamber with $CO_2$, the first position may be engaged, such that the first port of the valve base and the opening of the valve block are substantially aligned to allow the chamber to be loaded with $CO_2$, while the second port is isolated and/or closed from being in fluid communication with the chamber of the syringe. In one embodiment, the first position is engaged for approximately five seconds, although this measurement is not intended to be limiting. To deliver a bolus of $CO_2$ to the patient, the force may be released to engage the device in the second position, such that the second port of the valve base is substantially aligned with the opening of the valve block, while the first port is isolated and/or closed from being in fluid communication with the chamber of the syringe.

In another embodiment, to load the chamber of the syringe with $CO_2$, the first position may be engaged, such that the first port of the valve block and the opening of the valve base are substantially aligned to allow the chamber to be loaded with $CO_2$, while the second port is isolated and/or closed from being in fluid communication with the chamber of the syringe. In one embodiment, the first position is engaged for approximately five seconds, although this measurement is not intended to be limiting. To deliver a bolus of $CO_2$ to the patient, the force may be released to engage the device in the second position, such that the second port of the valve block is substantially aligned with the opening of the valve base, while the first port is isolated and/or closed being in fluid communication with the chamber of the syringe.

The devices and systems, as described herein, may be configured so as to allow for single-handed operation of the $CO_2$ delivery devices to deliver one or more boli of $CO_2$ to a subject. The configuration of $CO_2$ delivery devices described herein reduces or eliminates the need for dual-handed operation of the $CO_2$ delivery devices to deliver one or more boli of $CO_2$ to a subject. To deliver a bolus of $CO_2$ in accordance with the exemplary devices and systems disclosed herein, a user can grasp or hold a $CO_2$ delivery device in the first position with one hand and actuate the device with the same hand to engage the device in a second position, so as to deliver a bolus of $CO_2$ to a subject.

It will be readily understood with the aid of the present disclosure that the components of the embodiments, as generally described and illustrated in the figures herein, could be arranged and designed in a variety of configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

FIG. 1 provides a schematic illustration of an embodiment of a system suited to the methods for delivering $CO_2$ as an angiographic contrast agent to a subject. Shown in FIG. 1 is a $CO_2$ supply assembly 140 comprising a pressure regulator 142, a sterile filter 144, a $CO_2$ gas supply line 146 and a gas sensor 148. In some embodiments, the pressure regulator 142 maintains the pressure of the $CO_2$ being delivered from the $CO_2$ source 150 to the syringe 120 at approximately 1.3 atm above normal atmospheric pressure. As will be appreciated, a gas sensor 148 may be included in the $CO_2$ supply assembly 140 to ensure that the gas being delivered to the subject is $CO_2$ gas and not a gas other than $CO_2$. In some embodiments, the gas sensor 148 may be included in the $CO_2$ supply assembly 140 to ensure that the $CO_2$ gas being delivered to the subject is not contaminated with a gas other than $CO_2$. In an embodiment, the gas sensor 148 may be an $O_2$ gas sensor.

As illustrated in FIG. 1, the $CO_2$ gas supply line 146 of the $CO_2$ supply assembly 140 may be coupled to a $CO_2$ delivery device 130, which includes a shuttle valve assembly 100 attached to a syringe 120. The shuttle valve assembly 100 includes a valve base 116 that is connected or otherwise attached to a valve block 101. The shuttle valve assembly 100 is attached to the syringe 120, such that the longitudinal axis of the shuttle valve assembly 100 is perpendicular to the longitudinal axis of the syringe 120. In some embodiments, as shown herein, the syringe 120 includes a plunger 124 with threads 126 spirally disposed over the cylindrical surface of the plunger 124 and a chamber 122 configured to receive the threaded plunger 124. The syringe 120 may be configured to include a thread-receiving member 128 at the base of the chamber 122 to retain the threaded plunger 124, so as to allow tunable adjustment of the volume of the chamber 122. In an alternative embodiment, the syringe 120 may be configured to have a predetermined volume. In certain embodiments, the first port 102 and the second port 104 on the valve base 116 may be coupled to a $CO_2$ gas supply line 146 and a connection line 110, respectively. The connection line 110 may include an outlet 112 for coupling to a catheter (not shown) for delivery of $CO_2$ to the patient.

It will be appreciated by those of skill in the art having the benefit of this disclosure that this order may be modified. For example, the gas sensor 148 may be positioned between the pressure regulator 142 and the sterile filter 144 and/or the $CO_2$ delivery system may be in accordance with another embodiment disclosed herein. It can also be appreciated that the schematic illustration of the embodiment of the system described herein may be modified to include additional $CO_2$ sources 150, sterile filters 144, $CO_2$ gas supply lines 146 and/or gas sensors 148. As will be appreciated, the one or more gas sensors 148 may be integrated into the $CO_2$ delivery device 130 and/or system. In certain embodiments, the one or more gas sensor 148 may be integrated with the shuttle valve assembly 100, the chamber 122, the plunger 124, the connection line 110, or other parts of the $CO_2$ delivery device 130 and/or system that may be directly or indirectly coupled to the subject, such that leaks and/or compromised parts in the $CO_2$ delivery device 130 and/or system may be detected or identified.

Figure 2:
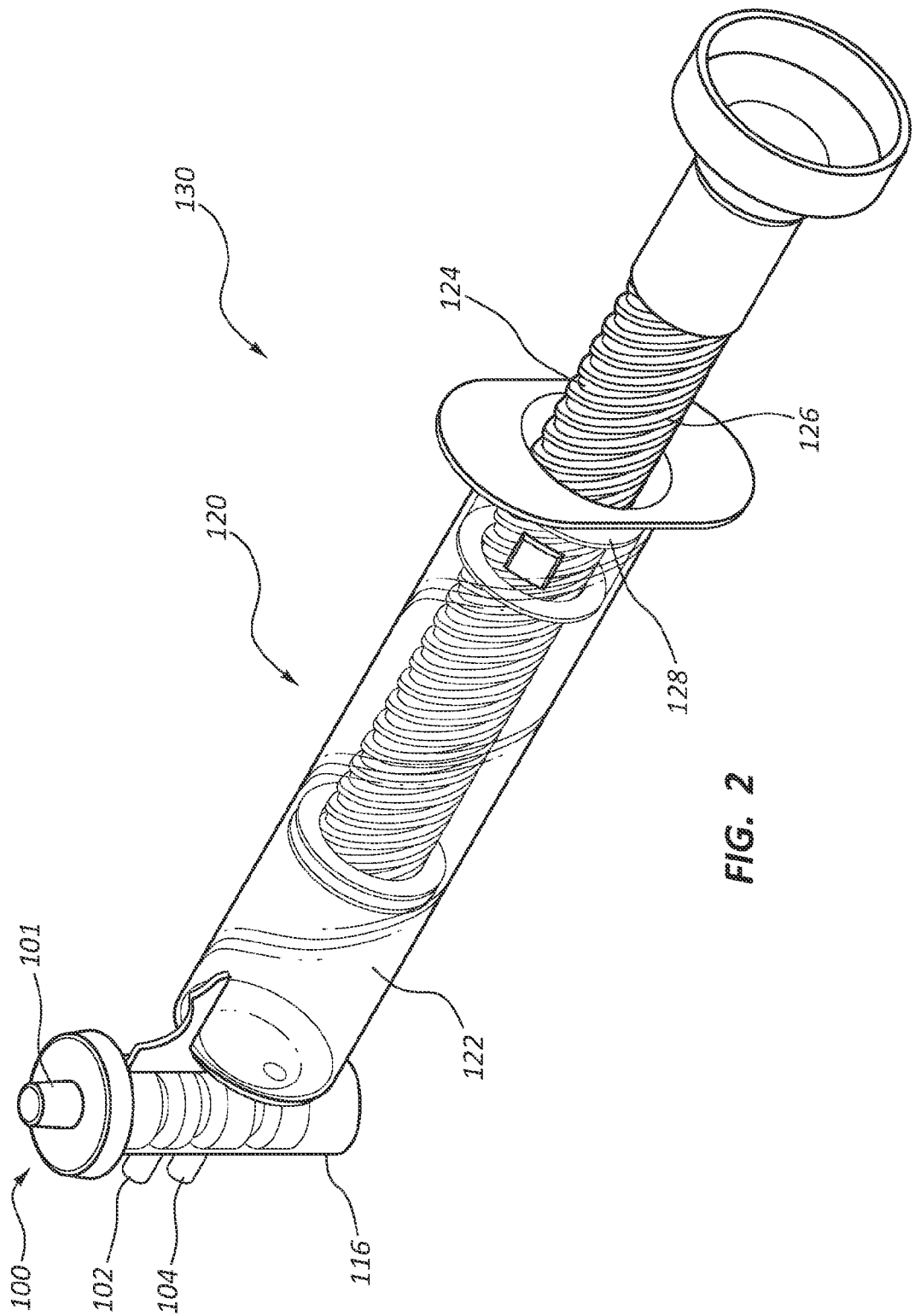
FIG. 2 is a rear perspective view of one embodiment of a $CO_2$ delivery device 130 that includes a shuttle valve assembly 100 connected to and in fluid communication with a syringe 120, which may be used by the methods and systems disclosed herein.

FIGS. 2-4 provide rear perspective, side, and cross sectional views of an exemplary $CO_2$ delivery device 130 in the first position, respectively. Shown in FIGS. 2-4 is a $CO_2$ delivery device 130 having a shuttle valve assembly 100 and a syringe 120 in the first position.

As illustrated in this embodiment, the shuttle valve assembly 100 may include a valve base 116 having a first port 102 and a second port 104, a valve block 101 having an opening 105, and a biasing member 106. The valve block 101 is connected to and substantially received by the valve base 116, such that the longitudinal axes of the valve block 101 and the valve base 116 are substantially collinear. As further illustrated in FIG. 4, the shuttle valve assembly 100 may include one or more circular sealing members 117. In some embodiments, the one or more circular sealing members 117 may be an o-ring. In an embodiment, the valve block 101 is substantially received by the valve base 116, such that the one or more circular sealing members 117 are disposed between the valve block 101 and the valve base 116. The syringe 120 connected to the shuttle valve assembly 100 may include a chamber 122 and a plunger 124, wherein the chamber 122 is configured to receive the plunger 124. As illustrated in FIGS. 2-4, the shuttle valve assembly 100 is connected to the syringe 120, such that the longitudinal axis of the shuttle valve assembly 100 is substantially perpendicular to the longitudinal axis of the syringe 120. The first port 102 and the second port 104 may be positioned substantially adjacent to each other and may protrude along the radius of the valve base 116, such that the longitudinal axes of the first port 102 and the second port 104 are substantially perpendicular to the longitudinal axis of the shuttle valve assembly 100. In some embodiments, the longitudinal axes of the first port 102 and the second port 104 may be substantially collinear with the longitudinal axis of the syringe 120.

To maintain the $CO_2$ delivery device 130 in the first position, a biasing member 106 may be disposed between the valve block 101 and the valve base 116, such that the opening 105 of the valve block 101 is substantially aligned with the first port 102, while the second port 104 is isolated and/or closed from being in fluid communication with the chamber 122 of the syringe 120. In some embodiments, the second port 104 may be isolated between two circular sealing members 117 when the $CO_2$ delivery device 130 is maintained in the first position. Examples of mechanisms suitable for use as a biasing member 106 include compression springs, volute springs, and the like. When the $CO_2$ delivery device 130 is in the first position, the substantial alignment of the first port 102 with the opening 105 of the valve block 101 allows the chamber 122 of the syringe 120 to be in fluid communication with the first port 102, such that the first port 102 may be directly or indirectly coupled to a $CO_2$ source (as illustrated in FIG. 1) to load the chamber 122 of the syringe 120 with $CO_2$.

Figure 5:
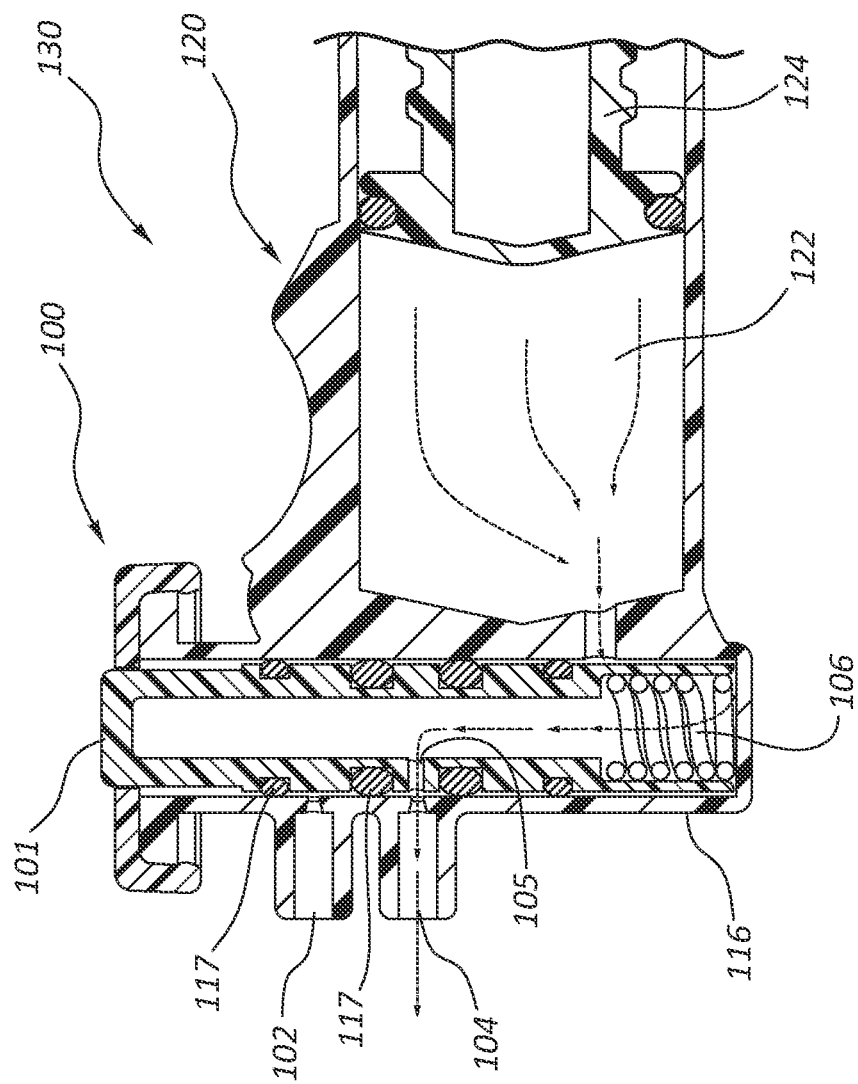
FIG. 5 is an enlarged, partially cut-away cross sectional view of a shuttle valve assembly 100 connected to a syringe 120. This enlarged cross sectional view illustrates the $CO_2$ delivery device 130 in a second position, such that the chamber 122 of the syringe 120 is in fluid communication with the second port 104 of the shuttle valve assembly 100.

FIG. 5 provides an enlarged cross sectional view of a $CO_2$ delivery device 130 illustrated in FIGS. 2-4, wherein the $CO_2$ delivery device 130 is engaged in the second position. To engage the $CO_2$ delivery device 130 in the second position, a force (illustrated as $F_1$ in FIG. 4) may be applied to the valve block 101 against the biasing member 106, such that the valve block 101 slides toward the biasing member 106. When engaged in the second position, the opening 105 of the valve block 101 is substantially aligned with the second port 104 of the valve base 116, while the first port 102 of the valve base 116 is isolated and/or closed from being in fluid communication with the chamber 122 of the syringe 120. In an embodiment, the first port 102 of the valve base 116 may be isolated between two circular sealing members 117 when the $CO_2$ delivery device 130 is engaged in the second position. As illustrated in FIG. 5, the chamber 122 of the syringe 120 is in fluid communication with the second port 104 of the shuttle valve assembly 100. The second port 104 may be coupled to a connection line (not shown) suitable for delivering $CO_2$ to a subject. When the $CO_2$ delivery device 130 is engaged in the second position, the $CO_2$ in the chamber 122 of the syringe 120 may be delivered to the subject.

As illustrated herein, the syringe 120 may be configured to include a threaded plunger 124 and a chamber 122 suitable for receiving a threaded plunger 124. In one embodiment, the chamber 122 may include a thread-receiving member 128 that is configured to receive the threaded plunger 124, so as to allow for tunable adjustment of the volume of the chamber 122. As will be appreciated, a threaded plunger 124 and a chamber 122 configured to receive a threaded plunger 124 allows for increased adjustability of the volume of $CO_2$ within the syringe 120, and allows the user greater control over the volume of $CO_2$ to be administered to the subject. Furthermore, a threaded plunger 124 may also prevent a practitioner from inadvertently delivering an explosive bolus to a patient by translating the plunger too rapidly.

In an alternative embodiment, the syringe 120 may be configured to have a predetermined volume. The syringe 120 may be configured to hold a volume ranging from about 1 cc to about 200 cc, although these values are not intended to be limiting. In certain embodiments, the syringe 120 may be configured to hold a volume ranging from about 1 cc to about 150 cc, about 1 cc to about 100 cc, about 20 cc to about 100 cc, about 20 cc to about 80 cc, and about 20 cc to about 60 cc. As will be appreciated, these values may be tunably adjusted to accommodate greater or smaller volumes within the chamber 122 of the syringe 120. If desired, a practitioner may further or fully empty the chamber 122 of the syringe 120 by actuating the plunger 124.

In accordance with the embodiment as provided herein, a user may hold the $CO_2$ delivery device 130 single-handedly by grasping the outer surface of the syringe chamber 122, such that the shuttle valve assembly 100 points away from the user, and the valve block 116 faces upward. To deliver one or more boli of $CO_2$ using the $CO_2$ delivery device 130, a user may apply a force (illustrated as $F_1$ in FIG. 4) with their thumb to the valve block 116 against the biasing member 106, so as to engage the $CO_2$ delivery device 130 in a second position.

Figure 6:
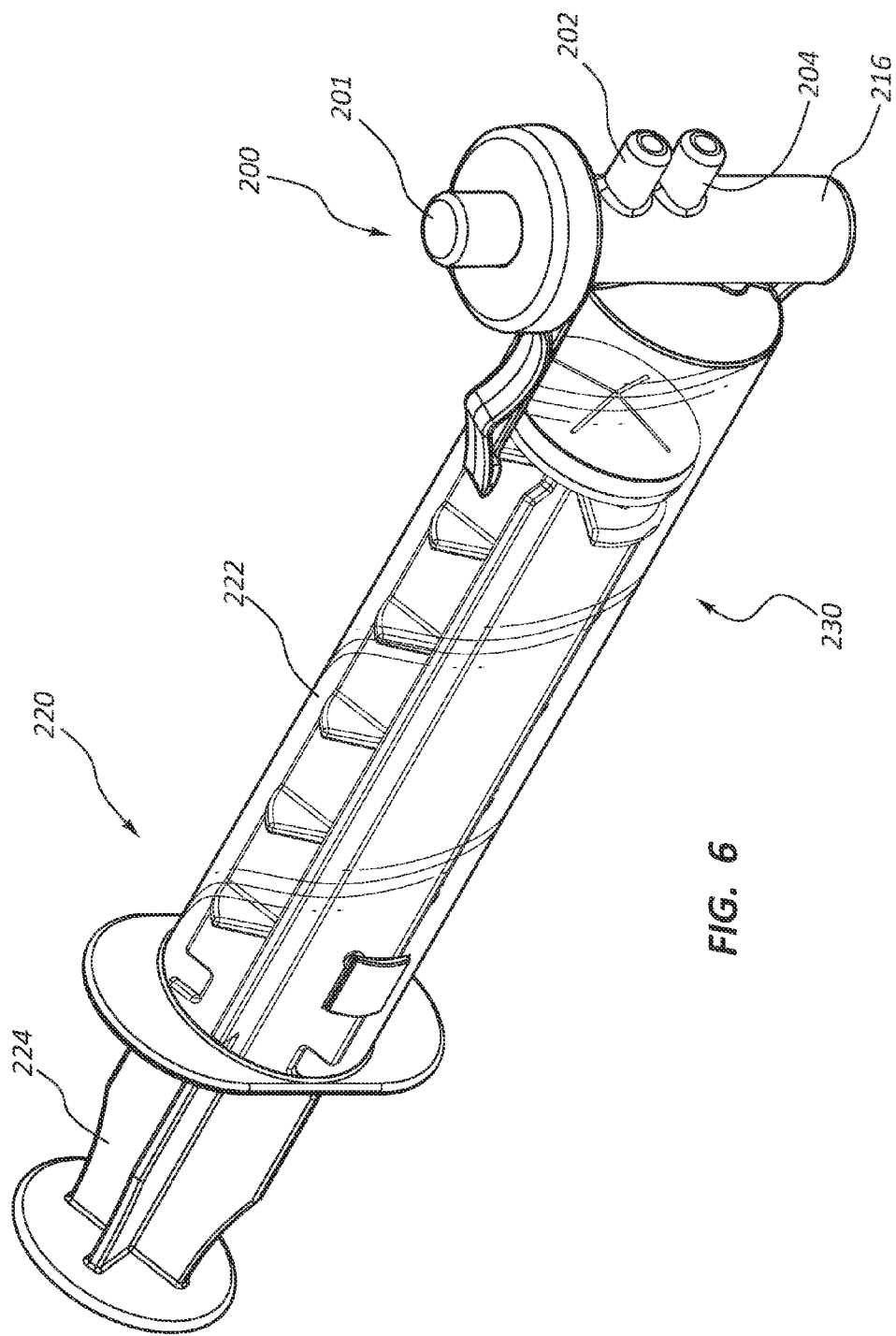
FIG. 6 is a front perspective view of another embodiment of a $CO_2$ delivery device 230, illustrating an alternative design of the syringe 220.
Figure 9:
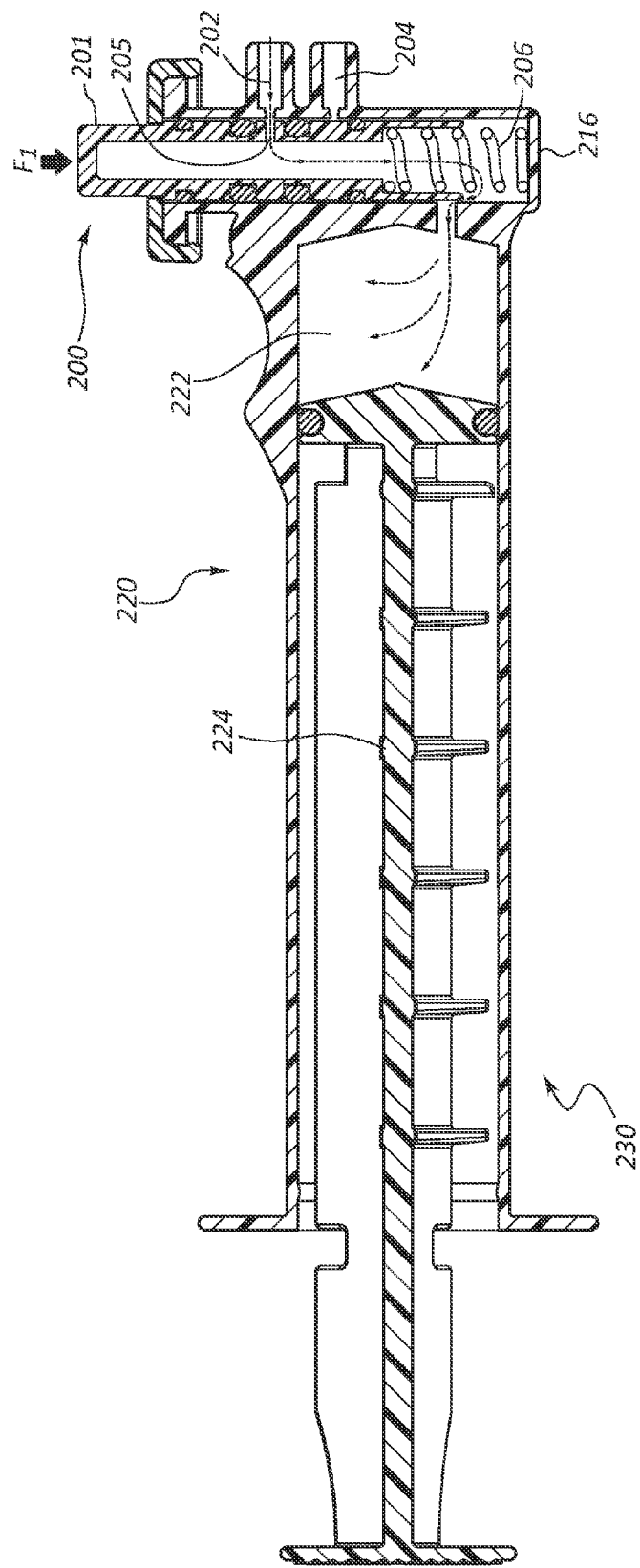
FIG. 9 is a cross sectional view of the $CO_2$ delivery device 230 of FIG. 7. This cross sectional view illustrates the $CO_2$ delivery device 230 in a first position, such that the chamber 222 of the syringe 220 is in fluid communication with the first port 202 of the shuttle valve assembly 200.

FIGS. 6, 7 and 9 provide front perspective, side, and cross sectional views of an exemplary $CO_2$ delivery device 230, respectively. Shown in FIGS. 6, 7 and 9 is a $CO_2$ delivery device 230 having a shuttle valve assembly 200 and a syringe 220 in the first position.

The shuttle valve assembly 200 may include a valve base 216 having a first port 202 and a second port 204, a valve block 201 having an opening 205, and a biasing member 206. The valve block 201 is connected to and substantially received by the valve base 216, such that the longitudinal axes of the valve block 201 and valve base 216 are substantially collinear. As further illustrated in FIG. 9, the shuttle valve assembly 200 may include one or more circular sealing members 217. In an embodiment, the valve block 201 and the valve base 216 are both substantially cylindrical. In some embodiments, the valve block 201 is substantially received by the valve base 216, such that the one or more circular sealing members 217 are disposed between the valve block 201 and the valve base 216. The syringe 220 connected to the shuttle valve assembly 200 may include a chamber 222 and a plunger 224, wherein the chamber 222 is configured to receive the plunger 224. As illustrated in FIGS. 6, 7 and 9, the shuttle valve assembly 200 is connected to the syringe 220, such that the longitudinal axis of the shuttle valve assembly 200 is substantially perpendicular to the longitudinal axis of the syringe 220. The syringe 220 may include a plunger 224 (that may optionally be threaded) and a chamber 222 configured to receive the plunger 224. In one embodiment, the syringe 220 may be configured to have a predetermined volume. The first port 202 and the second port 204 may be positioned substantially adjacent to each other and may protrude along the radius of the valve base 216, such that the longitudinal axes of the first port 202 and the second port 204 are substantially perpendicular to the longitudinal axis of the shuttle valve assembly 200. In certain embodiments, the longitudinal axes of the first port 202 and the second port 204 may be substantially parallel to the longitudinal axis of the syringe 220.

To maintain the $CO_2$ delivery device 230 in the first position, a biasing member 206 may be disposed between the valve block 201 and the valve base 216, such that the opening 205 of the valve block 201 is substantially aligned with the first port 202, while the second port 204 is isolated and/or closed from being in fluid communication with the chamber 222 of the syringe 220. In some embodiment, the second port 204 of the valve base 216 may be isolated between two circular sealing members 217 when the $CO_2$ delivery device 230 is maintained in the first position. When maintained in the first position, the chamber 222 of the syringe 220 is in fluid communication with the first port 202, such that the first port 202 may be directly or indirectly coupled to a $CO_2$ source (as illustrated in FIG. 1) to load the chamber 222 of the syringe 220 with $CO_2$.

FIG. 8 provides a front view of one end of the exemplary $CO_2$ delivery device 230 of FIG. 6 in the first position. As shown in FIG. 8, the first port 202 and the second port 204 are positioned adjacent to each other, such that both the first port 202 and the second port 204 are protruding from the valve base 216 along the sagittal plane (indicated as 9 in FIG. 8) of the $CO_2$ delivery device 230.

Figure 10:
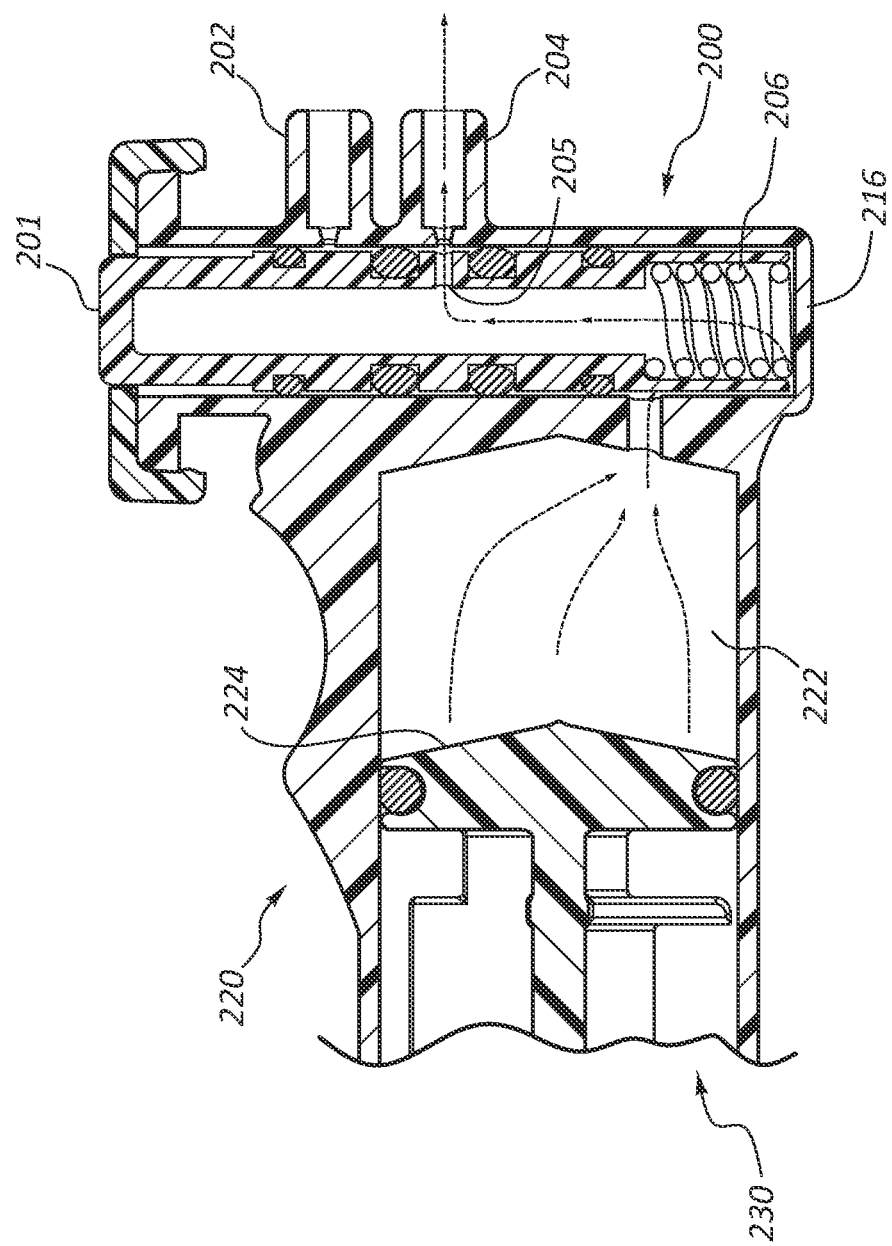
FIG. 10 is an enlarged, partially cut away cross sectional view of a shuttle valve assembly 200 connected to a syringe 220. This enlarged cross sectional view illustrates the $CO_2$ delivery device 230 in a second position, such that the chamber 222 of the syringe 220 is in fluid communication with the second port 204 of the shuttle valve assembly 200.

FIG. 10 provides an enlarged cross sectional view of the $CO_2$ delivery device 230 illustrated in FIGS. 6-9, wherein the $CO_2$ delivery device 230 is engaged in the second position. To engage the $CO_2$ delivery device 230 in the second position, a force (illustrated as $F_1$ in FIG. 9) may be applied to the valve block 201 against the biasing member 206, such that the valve block 201 slides toward the biasing member 206. When engaged in the second position, the opening 205 of the valve block 201 is substantially aligned with the second port 204 of the valve base 216, such that the chamber 222 of the syringe 220 is in fluid communication with the second port 204 of the shuttle valve assembly 200, while the first port 202 is isolated and/or closed from being in fluid communication with the chamber 222 of the syringe 220. In an embodiment, the first port 202 may be isolated between two circular sealing members 217 when the $CO_2$ delivery device 230 is engaged in the second position. The second port 204 may be coupled to a connection line (not shown) suitable for delivering $CO_2$ to a subject. When the $CO_2$ delivery device 230 is engaged in the second position, the $CO_2$ in the chamber 222 of the syringe 220 may be delivered to the subject.

In accordance with the embodiment as provided herein, a user may hold the $CO_2$ delivery device 230 single-handedly by grasping the outer surface of the syringe chamber 222, such that the shuttle valve assembly 200 points away from the user and the valve block 216 faces upward. To deliver one or more boli of $CO_2$ using the $CO_2$ delivery device 230, a user may apply a force (illustrated as $F_1$ in FIG. 9) with their thumb to the valve block 216 against the biasing member 206, so as to engage the $CO_2$ delivery device 230 in a second position.

Figure 11:
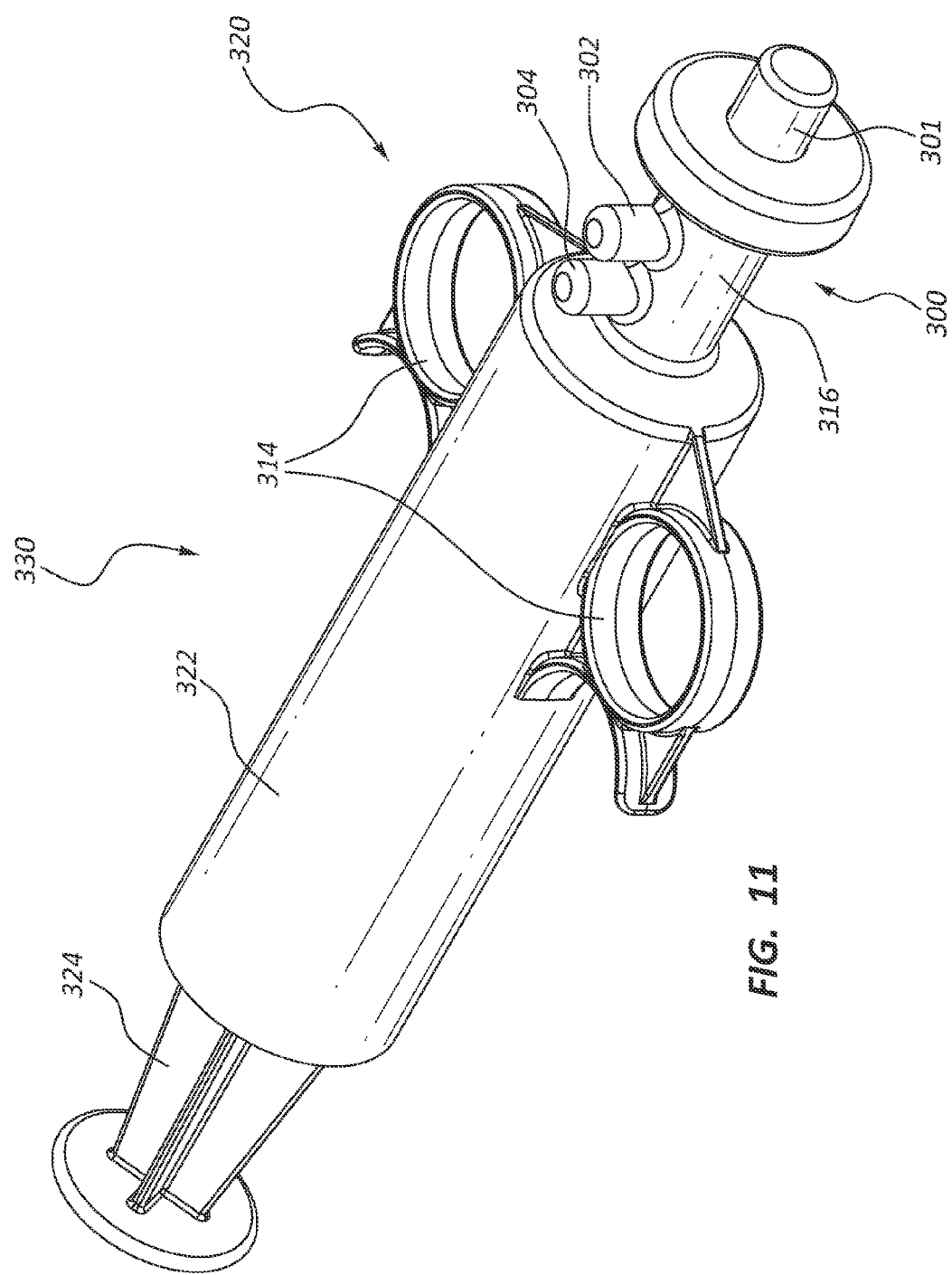
FIG. 11 is a front perspective view of one embodiment of a $CO_2$ delivery device 330. This front perspective view illustrates finger-receiving portions 314 that are attached to the exterior cylindrical surface of the chamber 322.
Figure 12:
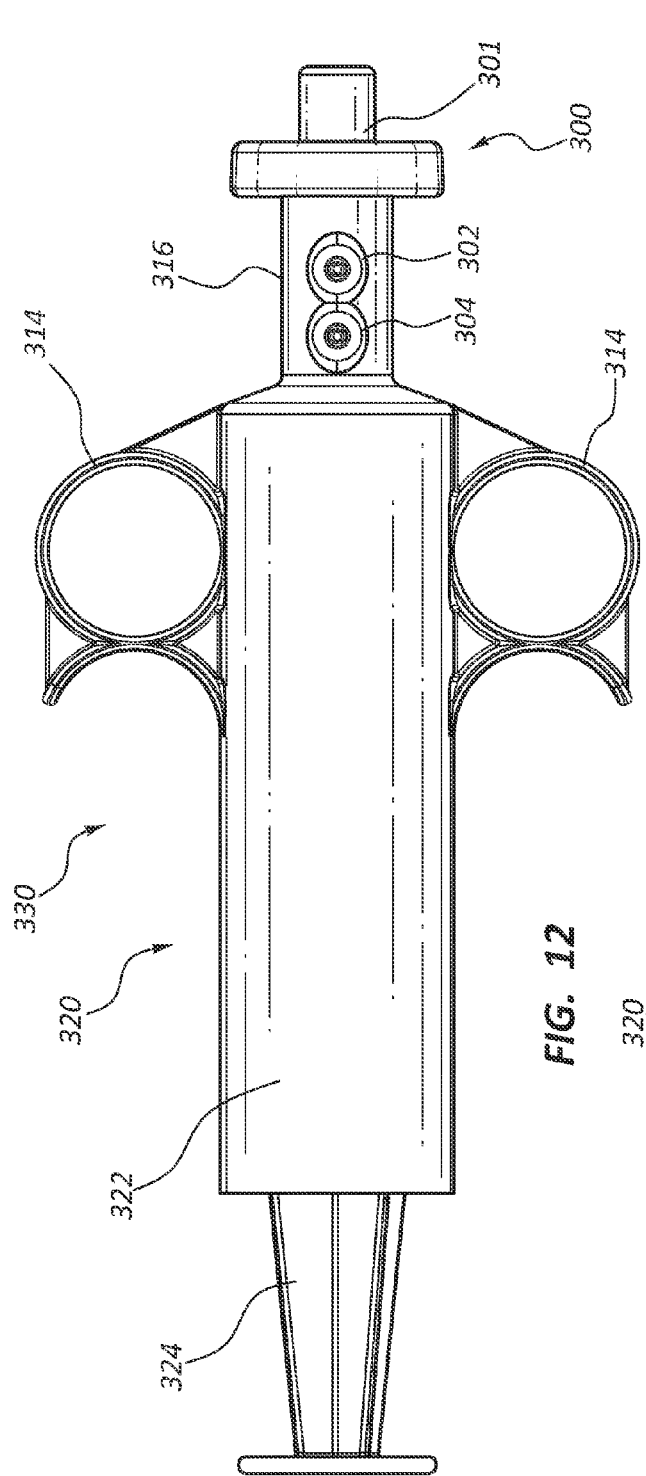
FIG. 12 is a top view of the $CO_2$ delivery device 330 of FIG. 11.
Figure 13:
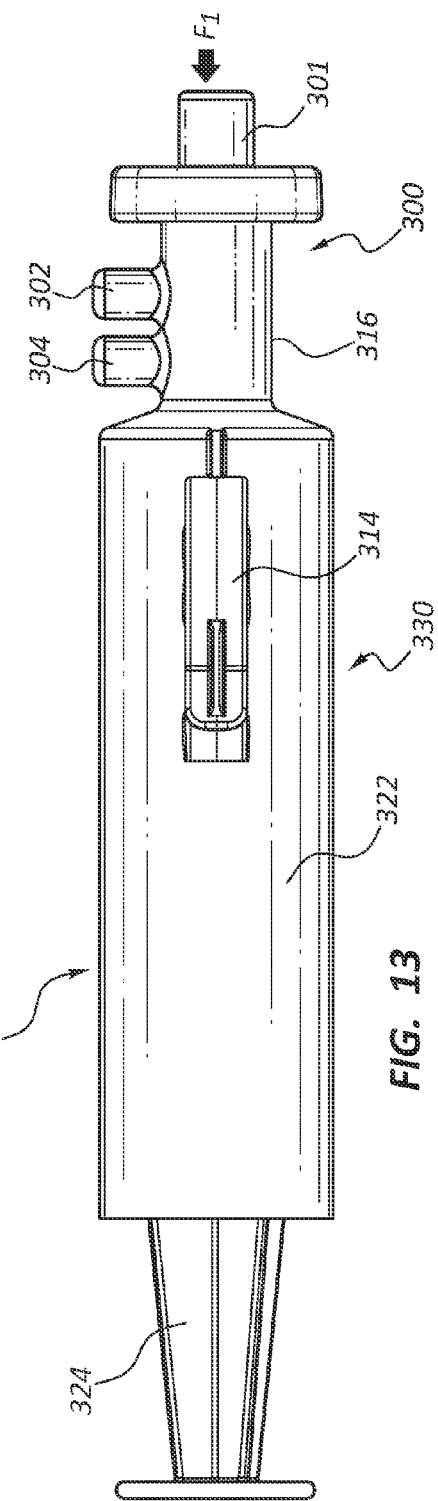
FIG. 13 is a side view of the $CO_2$ delivery device 330 of FIG. 11.

FIGS. 11-13 provide front perspective, top and side views, respectively, of an exemplary $CO_2$ delivery device 330 in the first position. Shown in FIGS. 11-13 is a $CO_2$ delivery device 330 that includes two finger-receiving mechanisms 314 that are attached to the outer surface of the chamber 322 of the syringe 320.

The finger-receiving mechanisms 314 are configured such that a user may hold the $CO_2$ delivery device 330 with one hand for single-handed operation of the device 330. In one embodiment, both of the finger-receiving mechanisms 314 are attached to syringe 320 on the coronal plane of the $CO_2$ delivery device 330 and positioned adjacent to the shuttle valve assembly 300. As illustrated in FIGS. 11-13, the shuttle valve assembly 300 is connected to the syringe 320, such that the longitudinal axis of the shuttle valve assembly 300 is collinear with the longitudinal axis of the syringe 320. As described in previous embodiments, the syringe 320 may include a threaded plunger 324 and a chamber 322 configured to receive the threaded plunger. In one embodiment, the syringe 320 may be configured to have a predetermined volume. As will be appreciated, the actual volume dispensed to the subject is dependent on the gas pressure and the predetermined volume of the syringe 320. In some embodiments, the practitioner may adjust the volume of $CO_2$ delivered to the patient by adjusting the gas pressure and/or the predetermined volume of the syringe 320.

FIG. 14 provides a top view of one end of the $CO_2$ delivery device 330. As shown in FIG. 14, both of the finger-receiving mechanisms 314 are attached to the syringe 320 on the coronal plane of the $CO_2$ delivery device 330.

FIG. 15 illustrates a cross sectional view of the $CO_2$ delivery device 330 in a first position. As shown in FIG. 15, the shuttle valve assembly 300 may include one or more circular sealing members 317. In some embodiments, the valve block 301 is substantially received by the valve base 316, such that the one or more circular sealing members 317 are disposed between the valve block 301 and the valve base 316. To maintain the $CO_2$ delivery device 330 in the first position, a biasing member 306 may be disposed between the valve block 301 and the valve base such that the opening 305 of the valve block 301 is substantially aligned with the first port 302, while the second port 304 is isolated and/or closed from being in fluid communication with the chamber 322 of the syringe 320. In an embodiment, the second port 304 may be isolated between two circular sealing member 317 when the $CO_2$ delivery device 330 is maintained in the first position. The substantial alignment of the first port 302 with the opening 305 of the valve block 301 allows the chamber 322 of the syringe 320 to be in fluid communication with the first port 302, such that the first port 302 may be directly or indirectly coupled to a $CO_2$ source (as illustrated in FIG. 1) to load the chamber 322 of the syringe 320 with $CO_2$.

FIG. 16 illustrates an enlarged cross sectional view of the $CO_2$ delivery device 330 provided in FIGS. 11-15, wherein the $CO_2$ delivery device 330 is engaged in a second position. To engage the $CO_2$ delivery device 330 in the second position, a force (illustrated as $F_1$ in FIG. 15) may be applied to the valve block 301 against the biasing member 306, such that the valve block 301 moves toward the biasing member 306. When the $CO_2$ delivery device 330 is engaged in the second position, the opening 305 of the valve block 301 is substantially aligned with the second port 304 of the valve base 316, while the first port 302 is isolated and/or closed from being in fluid communication with the chamber 322 of the syringe 320. In an embodiment, the first port 302 is isolated between two circular sealing members 317 when the $CO_2$ delivery device 330 is engaged in the second position. As shown in FIG. 16, the chamber 322 of the syringe 320 is in fluid communication with the second port 304 of the shuttle valve assembly 300. The second port 304 may be coupled to a connection line (not shown) suitable for delivering $CO_2$ to a subject. When the $CO_2$ delivery device 330 is engaged in the second position, the $CO_2$ in the chamber 322 of the syringe 320 may be delivered to the subject.

In accordance with the embodiment as illustrated herein, a user may insert their index finger into one finger-receiving mechanism 314 and their middle finger into the other finger-receiving mechanism 314. To deliver one or more boli of $CO_2$ using the $CO_2$ delivery device 330, the user may apply a force (illustrated as $F_1$ in FIG. 15) to the valve block 301 using their thumb on the same hand as the index and middle fingers holding the finger-receiving mechanisms 314, so as to actuate the shuttle valve assembly 300 and engage the $CO_2$ delivery device 300 in the second position.

Figure 17:
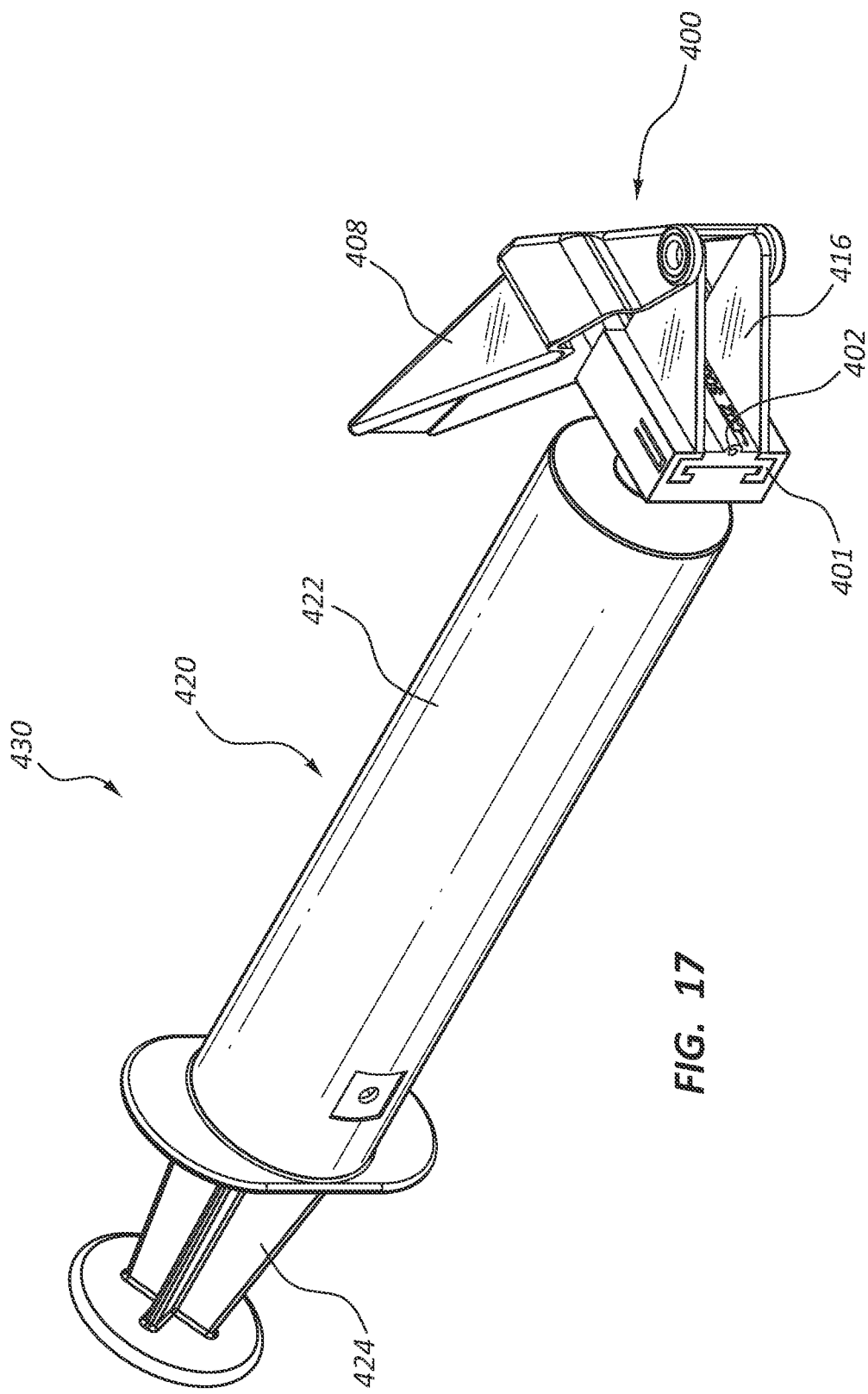
FIG. 17 is a front perspective view of another embodiment of a $CO_2$ delivery device 430, illustrating an alternative design of the shuttle valve assembly 400.
Figure 22:
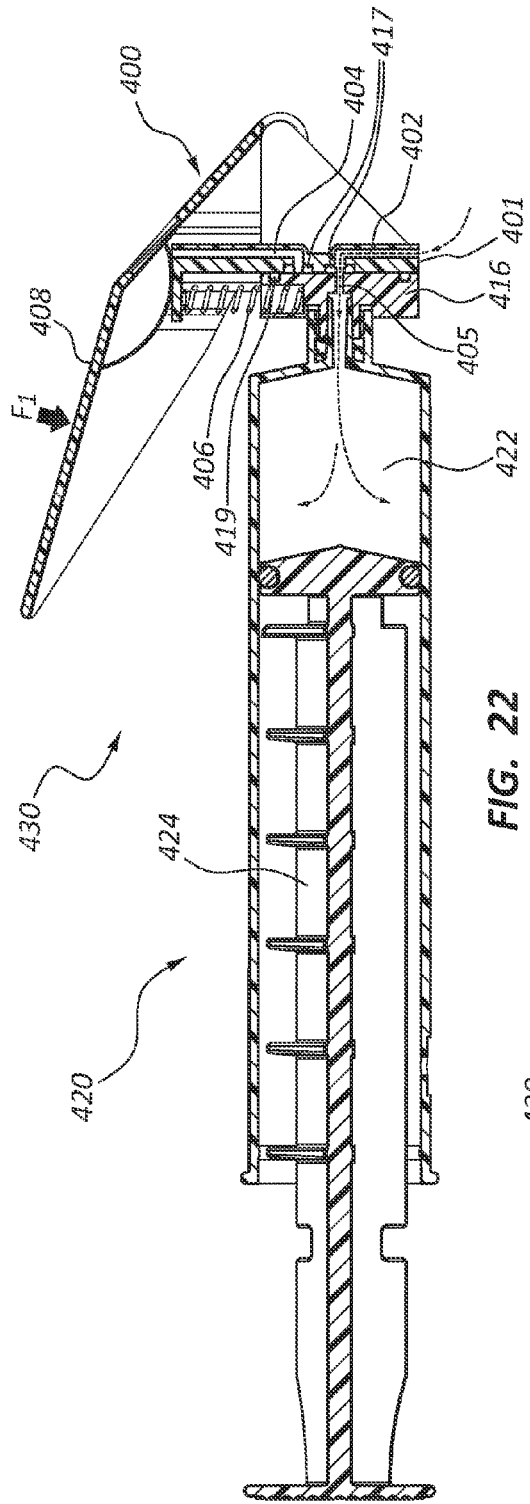
FIG. 22 is a cross sectional view of the $CO_2$ delivery device 430 of FIG. 19. This cross sectional view illustrates the $CO_2$ delivery device 430 in a first position, such that the chamber 422 of the syringe 420 is in fluid communication with the first port 402 of the shuttle valve assembly 400.

FIGS. 17, 19 and 22 provide front perspective, side, and cross sectional views, respectively, of an exemplary $CO_2$ delivery device 430 in the first position. Shown in FIGS. 17, 19 and 22 is a syringe 420 having a chamber 422 and a plunger 424, and a non-cylindrical shuttle valve assembly 400 that includes an actuating member 408, a valve block 401, and a valve base 416. As further illustrated in FIG. 22, the valve block 401 may include a first port 402 and a second port 404, and the valve base 416 may include an opening 405. As shown in FIG. 22, the non-cylindrical shuttle valve assembly 400 may also include a biasing member 406, one or more circular sealing members 417 and an elongated sealing member 419.

As illustrated herein, the valve block 401 may be configured to include a first port 402 and a second port 404, and the valve base 416 may be configured to include an opening 405. The valve block assembly 400 may be configured such that the valve block 401 is slidably attached to the valve base 416, such that a biasing member 406 may positioned between the valve block 401 and the valve base 416 to maintain the $CO_2$ delivery device 430 in the first position. The valve base 416 may be hingeably attached to an actuating member 408 that may be positioned adjacent to the valve block 401. When the $CO_2$ delivery device 430 is maintained in the first position, the opening 405 of the valve base 416 is substantially aligned with the first port 402, while the second port 404 is prevented from being in fluid communication with the chamber 422 of the syringe 420. In an embodiment, a circular sealing member 417 seals around the first port 402 when the first port 402 is substantially aligned with the opening 405, such that the second port 404 is not in fluid communication with the chamber 422 of the syringe 420 when the $CO_2$ delivery device 430 is in the first position. In certain embodiments, the second port 404 is isolated between the elongated sealing member 419 and the circular sealing member 417 sealing the first port 402 when the $CO_2$ delivery device 430 is in the first position. The substantial alignment of the first port 402 with the opening 405 of the valve base 416 allows the chamber 422 of the syringe 420 to be in fluid communication with the first port 402, such that the first port 402 may be directly or indirectly coupled to a $CO_2$ source (as illustrated in FIG. 1) to load the chamber 422 of the syringe 420 with $CO_2$. As described in previous embodiments, the syringe 420 may include a plunger 424 (optionally threaded) and a chamber 422 configured to receive the plunger 424. In one embodiment, the syringe 420 may be configured to have a predetermined volume.

Figure 18:
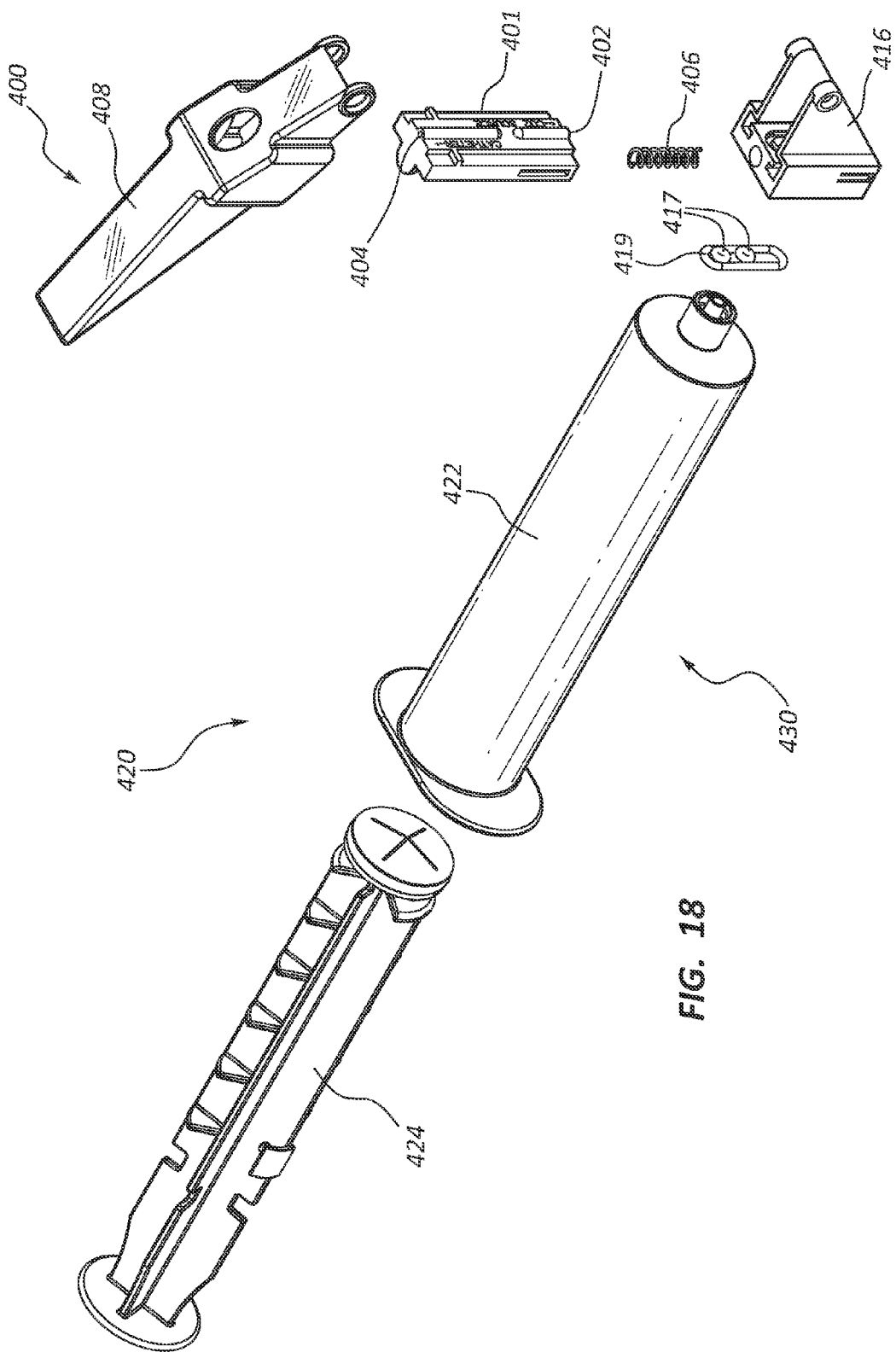
FIG. 18 is an exploded view of the $CO_2$ delivery device 430 of FIG. 17.

FIG. 18 illustrates an exploded view of the $CO_2$ delivery device 430 provided in FIGS. 17, 19 and 22. Shown in FIG. 18 is a syringe 420 having a chamber 422 and a plunger 424, an actuating member 408, a valve block 401 having a first port 402 and a second port 404, a valve base 416, a biasing member 406, two circular sealing members 417 and an elongated sealing member 419.

FIG. 20 provides a top view of one end of the exemplary $CO_2$ delivery device 430 of FIG. 17 in the first position. As shown in FIG. 20, the lengths of the first port 402 and the second port 404 are serially positioned along the sagittal plane (indicated as 22 in FIG. 20) of the valve block 401. The valve block 401 is slidably connected to the valve base 416, such that the valve block 401 slides along an axis that is substantially perpendicular to the longitudinal axis of the syringe 420.

FIG. 21 provides a bottom perspective view of the valve block 401 of the $CO_2$ delivery device 430. As illustrated in FIG. 21, the first port 402 and the second port 404 may be positioned adjacent to each other along the sagittal plane (indicated as plane 22 in FIG. 20) of the valve block 401.

Figure 23:
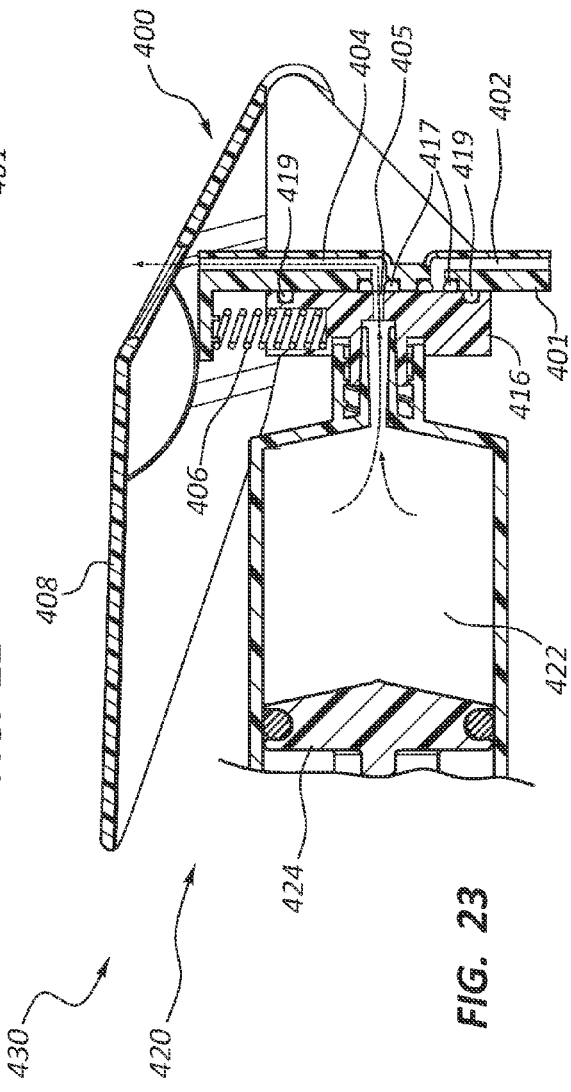
FIG. 23 is an enlarged, partially cut away cross sectional view of a shuttle valve assembly 400 connected to a syringe 420. This enlarged cross sectional view illustrates the $CO_2$ delivery device 430 in a second position, such that the chamber 422 of the syringe 420 is in fluid communication with the second port 404 of the shuttle valve assembly 400.

FIG. 23 illustrates an enlarged cross sectional view of the $CO_2$ delivery device 430 provided in FIGS. 17-20 and 22, wherein the $CO_2$ delivery device 430 is engaged in a second position. To engage the $CO_2$ delivery device 430 in the second position, a force (illustrated as $F_1$ in FIG. 19) may be applied to the actuating member 408 and/or the valve block 401 against the biasing member 406, such that the valve block 401 slides away from the actuating member 408. When the $CO_2$ delivery device 430 is engaged in the second position, the second port 404 is substantially aligned with the opening 405 of the valve base 416, while the first port 402 is prevented from being in fluid communication with the chamber 422 of the syringe 420. In an embodiment, a circular sealing member 417 seals around the second port 404 when the second port 404 is substantially aligned with the opening 405, such that the first port 402 is not in fluid communication with the chamber 422 of the syringe 420 when the $CO_2$ delivery device 430 is in the second position. In certain embodiments, the first port 402 is isolated between the elongated sealing member 419 and the circular sealing member 417 sealing the second port 404 when the $CO_2$ delivery device 430 is in the second position. When the $CO_2$ delivery device 430 is engaged in the second position, the chamber 422 of the syringe 420 is in fluid communication with the second port 404 of the shuttle valve assembly 400, such that the second port 404 may be coupled to a connection line (not shown) for the delivery of $CO_2$ to a subject.

In accordance with the embodiment as provided herein, a user may hold the $CO_2$ delivery device 430 single-handedly by grasping the outer surface of the syringe chamber 422, such that the shuttle valve assembly 400 is pointing upward. To deliver one or more boli of $CO_2$ using the $CO_2$ delivery device 430, a user may apply a force with their fingers or palm of their hand to the actuating member 408 and/or the valve block 416 against the biasing member 406, so as to engage the $CO_2$ delivery device 430 in a second position.

Figure 24:
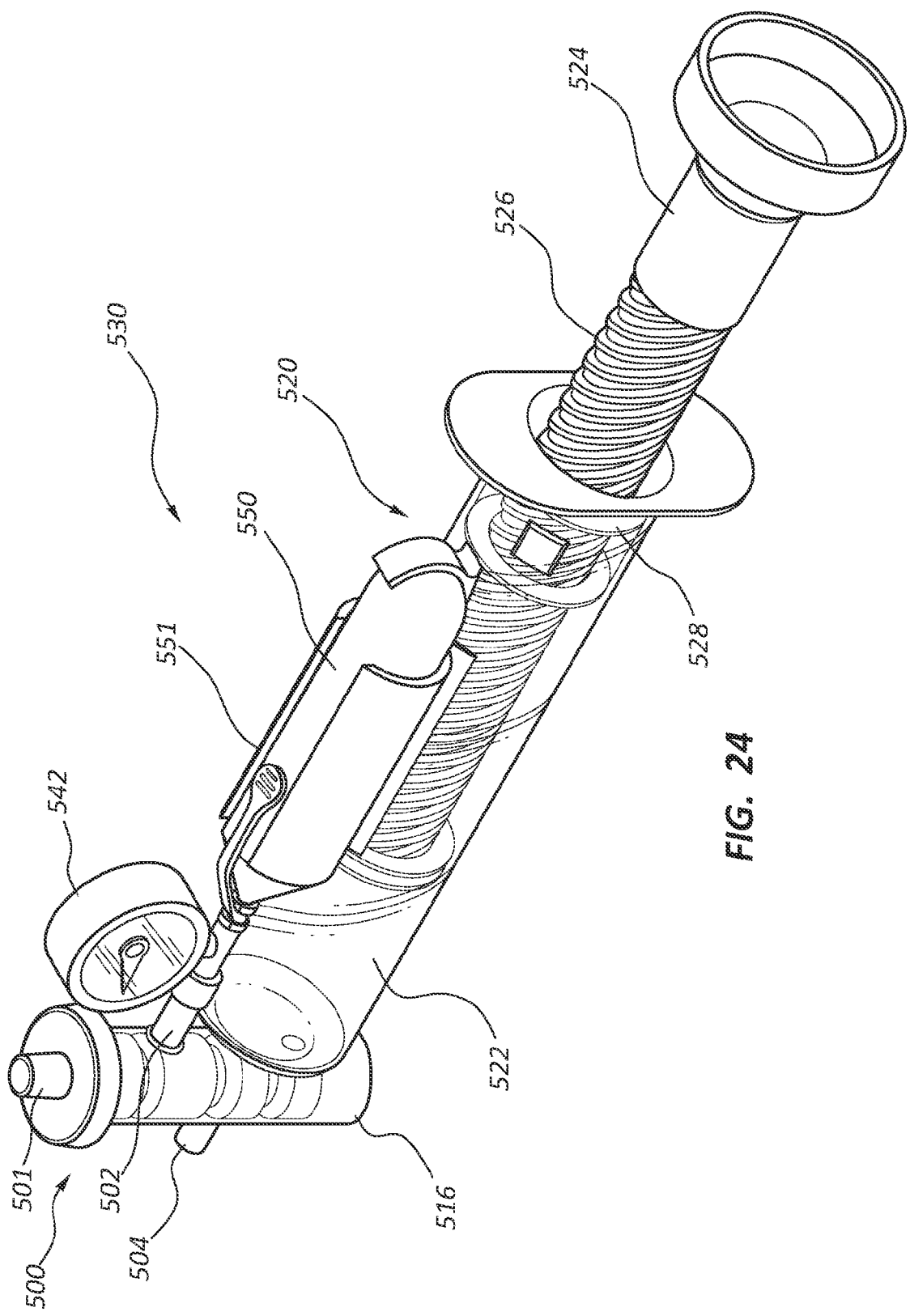
FIG. 24 is a rear perspective view of a $CO_2$ delivery device 530 with an integrated $CO_2$ source 550. This rear perspective view illustrates a $CO_2$ source 550 that is attached to the exterior cylindrical surface of the chamber 522 and connected first port 502 of the shuttle valve assembly 500, such that the chamber 522 of the syringe 520 is in fluid communication with the first port 502 of the shuttle valve assembly 500 and the $CO_2$ source 550.
Figures 25, 26:
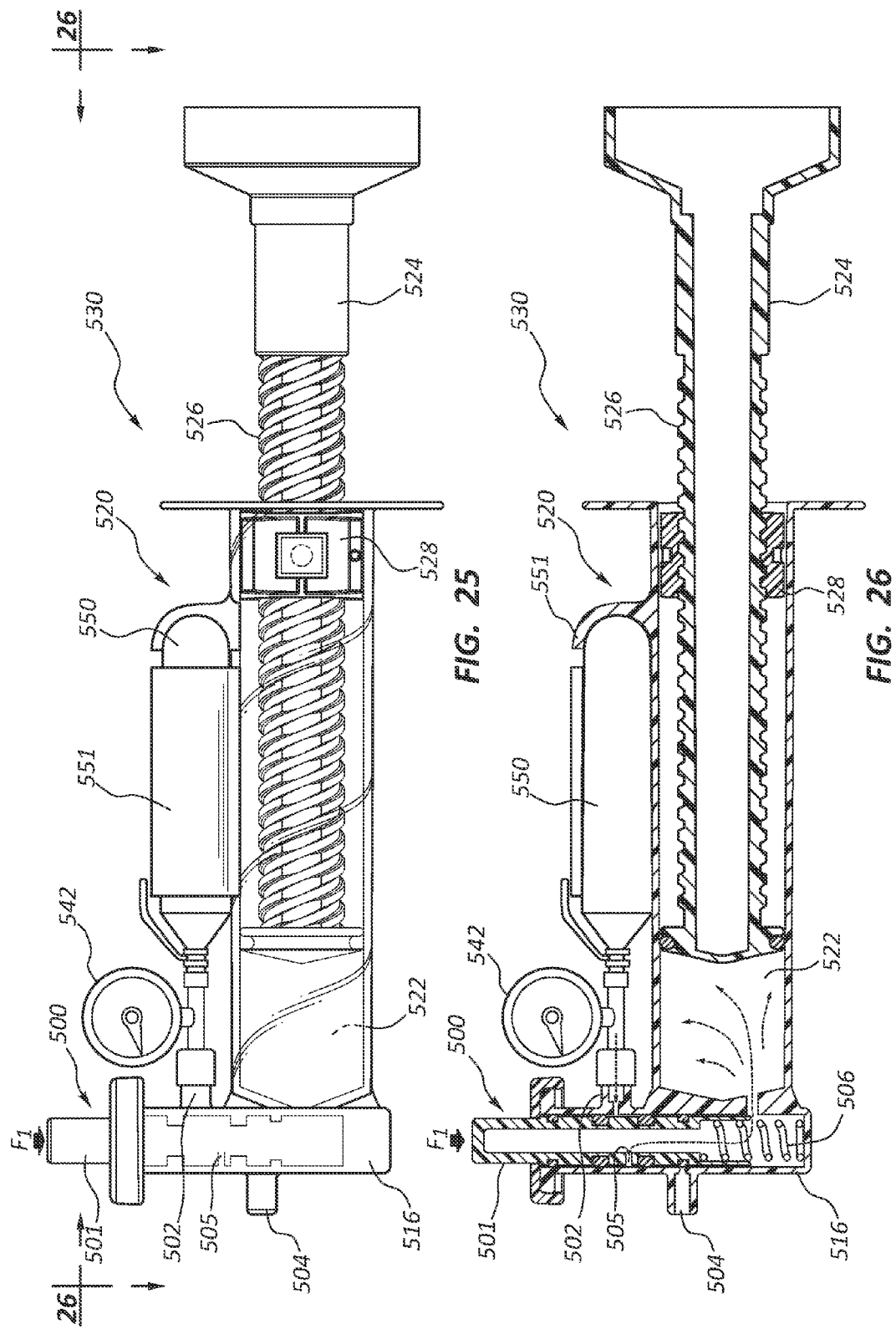
FIG. 25 is a side view of the $CO_2$ delivery device 530 of FIG. 24.
FIG. 26 is a cross sectional view of the $CO_2$ delivery device 530 of FIG. 25. This cross sectional view illustrates the $CO_2$ delivery device 530 in a first position, such that the chamber 522 of the syringe 520 is in fluid communication with the first port 502 of the shuttle valve assembly 500 and the $CO_2$ source 550.

FIGS. 24-26 provide rear perspective, side and cross sectional views, respectively, of an exemplary $CO_2$ delivery device 530 in the first position. Shown in FIGS. 24-26 is an integrated $CO_2$ source 550, integrated $CO_2$ source 550 retaining member 551, a pressure regulator 542, a syringe 520 having a chamber 522 and a plunger 524, a valve base 516 having a first port 502 and a second port 504, and a valve block 501. FIG. 26 further illustrates a biasing member 506, a plurality of circular sealing members 517, and a valve block 501 having an opening 505.

As illustrated herein, a $CO_2$ source 550 may be integrated with the $CO_2$ delivery device 530, such that the $CO_2$ source 550 is coupled to a pressure regulator 542, which is coupled to the first port 502 of the shuttle valve assembly 500. Examples of $CO_2$ sources 550 suitable for use in this context include $CO_2$ cartridges and the like. In an embodiment, the $CO_2$ source 550 may be a disposable $CO_2$ cartridge. In another embodiment, the $CO_2$ source 550 may be a reusable and/or refillable $CO_2$ cartridge. The $CO_2$ source 550 may be attached onto or integrated into the $CO_2$ delivery device 530. In some embodiments, the $CO_2$ source 550 may be attached to the chamber 522 of the syringe 520, such that the $CO_2$ source 550 is aligned along the longitudinal axis of the syringe 520. In still other embodiments, the $CO_2$ delivery device 530 may include a $CO_2$ source 550 retaining member 551 to hold or secure the $CO_2$ source 550 in place. As will be appreciated, an integrated $CO_2$ source 550 (e.g., $CO_2$ cartridge) eliminates the need for a user to locate and connect a $CO_2$ source 550 with the $CO_2$ delivery device 530. In addition, integrating a $CO_2$ source 550 into the $CO_2$ delivery device 530 reduces and/or eliminates the risk of accidental coupling to a source that is contaminated or that contains a gas or fluid other than $CO_2$.

The shuttle valve assembly 500 may be connected to the syringe 520, such that the longitudinal axis of the shuttle valve assembly 500 is perpendicular to the longitudinal axis of the syringe 520. The shuttle valve assembly 500 may include a valve base 516 having a first port 502 and a second port 504, a valve block 501 having an opening 505, and a biasing member 506. The valve block 501 may be connected to and substantially received by the valve base 516, such that the longitudinal axes of the valve block 501 and valve base 516 are substantially collinear. In an embodiment, the valve block 501 and the valve base 516 may both be substantially cylindrical. In certain embodiments, the valve block 501 may be substantially received by the valve base 516, such that a plurality of circular sealing members 517 are disposed between the valve block 501 and the valve base 516. The first port 502 and the second port 504 may protrude from the valve base 516 along the radius of the valve base 516, such that the first port 502 is substantially contralateral to the second port 504 and the longitudinal axes of the first port 502 and the second port 504 are substantially perpendicular to the longitudinal axis of the shuttle valve assembly. In certain embodiments, the longitudinal axes of the first port 502 and the second port 504 may be substantially collinear with the longitudinal axis of the syringe 520. The syringe 520 connected to the shuttle valve assembly 500 may include a chamber 522 and a plunger 524, wherein the chamber 522 is configured to receive the plunger 524. As described in previous embodiments, the syringe 520 may include a plunger 524 having threads 526 spirally disposed over the cylindrical surface of the plunger 524 and a chamber 522 configured to receive the threaded plunger 524. In an embodiment, a thread-receiving member 528 may be used to allow for incremental adjustability of the volume within the chamber 522 using the threaded plunger 524. In an alternative embodiment, the syringe 520 may be configured to have a predetermined volume, or may include a plunger 524 without threads 526.

When the $CO_2$ delivery device 530 is maintained in the first position, the opening to the first port 502 and the opening 505 of the valve block 501 are aligned between two circular sealing members 517, such that the $CO_2$ source 550 and the first port 502 are in fluid communication with the chamber 522 of the syringe 520, while the second port 504 is isolated and/or closed from being in fluid communication with the chamber 522 of the syringe 520. In some embodiments, the second port 504 may be isolated between two circular sealing members 517 when the $CO_2$ delivery device 130 is maintained in the first position.

Figure 27:
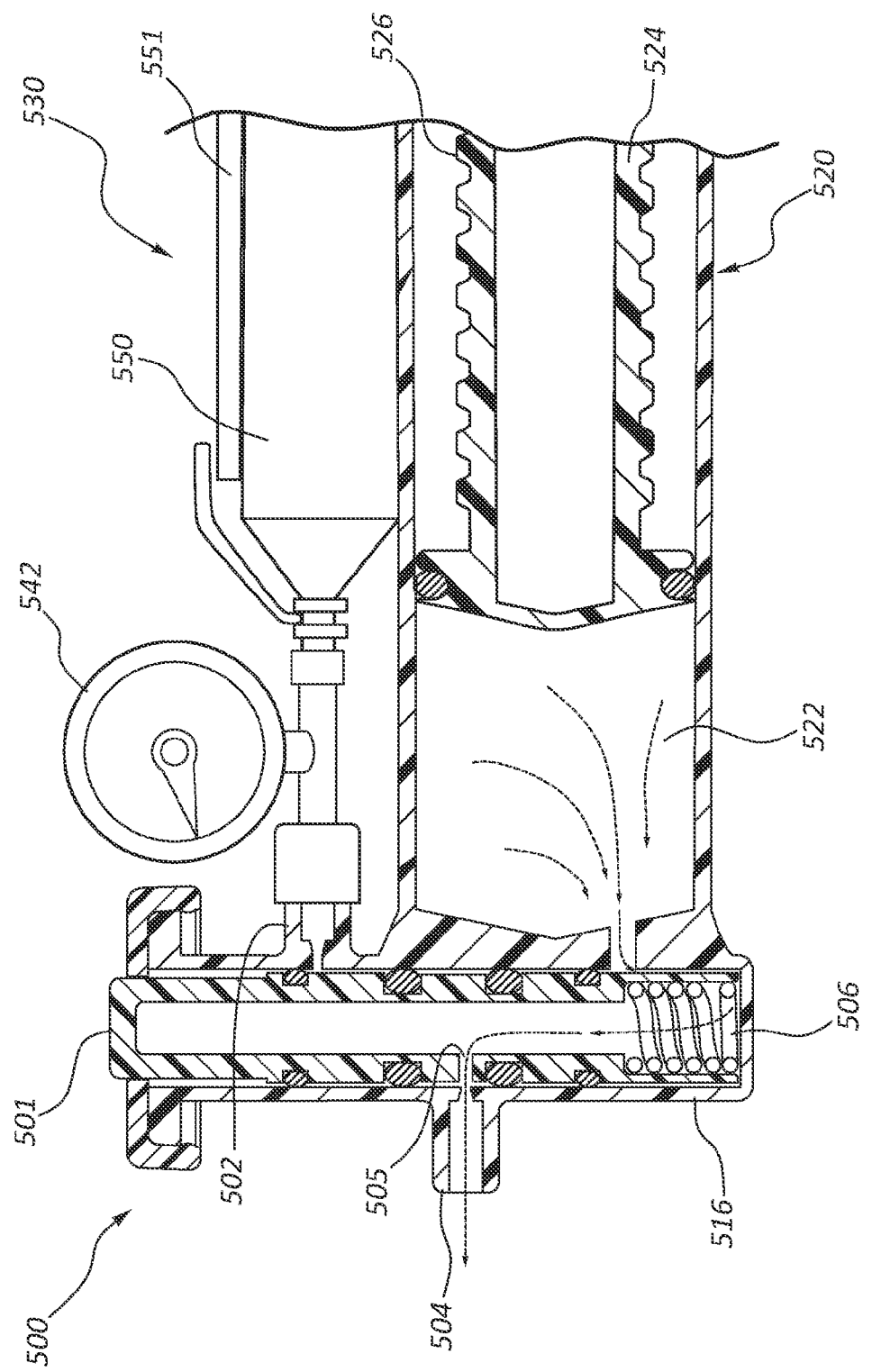
FIG. 27 is an enlarged, partially cut away cross sectional view of the $CO_2$ delivery device 530 of FIG. 26 in a second position, such that the chamber 522 of the syringe 520 is in fluid communication with the second port 504 of the shuttle valve assembly 500.

FIG. 27 provides an enlarged cross sectional view of the $CO_2$ delivery device 530 illustrated in FIGS. 24-26, wherein the $CO_2$ delivery device 530 is engaged in the second position. To engage the $CO_2$ delivery device 530 in the second position, a force (illustrated as $F_1$ in FIG. 25) may be applied to the valve block 501 against the biasing member 506, such that the valve block 501 slides toward the biasing member 506. When the $CO_2$ delivery device 530 is engaged in the second position, the second port 504 of the valve base 516 is substantially aligned with the opening 505 of the valve block 501, such that the chamber 522 of the syringe 524 is in fluid communication with the second port 504, while the first port 504 is isolated and/or closed from being in fluid communication with the chamber 522 of the syringe 524. In some embodiments, the first port 504 is isolated between two circular sealing members 517 when the $CO_2$ delivery device 530 is in the second position. The second port 504 may be coupled to a connection line (not shown) suitable for delivering $CO_2$ to a subject. When the $CO_2$ delivery device 530 is engaged in the second position, the $CO_2$ in the chamber 522 of the syringe 520 may be delivered to the subject.

In accordance with the embodiment as provided herein, a user may hold the $CO_2$ delivery device 530 single-handedly by grasping the outer surface of the syringe chamber 522, such that the shuttle valve assembly 500 points away from the user and the valve block 516 faces upward. To deliver one or more boli of $CO_2$ using the $CO_2$ delivery device 530, a user may apply a force with their thumb to the valve block 516 against the biasing member 506, so as to engage the $CO_2$ delivery device 530 in a second position.

As will be appreciated, the $CO_2$ delivery devices, in accordance with the embodiments described herein, may include tubing lines that are permanently bonded to the first port and the second port of the shuttle valve assembly. This allows a user to connect the tubing that leads to the first port to a $CO_2$ supply assembly or a $CO_2$ source. The user may also connect the tubing line that leads to the second port directly or indirectly to the subject.

The devices and systems disclosed herein may be pre-purged with $CO_2$ prior to packaging and/or use. As will be appreciated, the $CO_2$ delivery devices, in accordance with the embodiments as described herein, may be purged and/or loaded with $CO_2$ prior to use. Alternatively or in addition, in certain embodiments, the $CO_2$ delivery device may be flushed and/or loaded with $CO_2$ prior to and/or during packaging. In such an embodiment, a user may open the packaging containing the device and connect the device to the $CO_2$ without having to flush and/or load the device with $CO_2$ prior to use. In still other embodiments, the $CO_2$ delivery devices permanently bonded to tubing lines can also be pre-purged with $CO_2$ prior to packaging and/or use.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification, are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, inventive aspects lie in a combination of fewer than all features of any single foregoing disclosed embodiment. It will be apparent to those having skill in the art that changes may be made to the details of the above-described embodiments without departing from the underlying principles set forth herein.

The invention claimed is:

1. A $CO_2$ delivery device, comprising:
   a syringe comprising a chamber; and
   a shuttle valve assembly in fluid communication with the chamber of the syringe, the shuttle valve assembly comprising:
      a valve block comprising a first opening;
      a valve base comprising a first port and a second port;
      a plurality of sealing members disposed between the valve block and the valve base; and
      a biasing member biased against the valve block,
   wherein when the $CO_2$ deliver device is in a first position the first opening is substantially aligned with the first port such that the first port and the chamber are in fluid communication and the second port is isolated between a first sealing member and a second sealing member such that the second port is not in fluid communication with the chamber, and wherein the biasing member biases the valve block into the first position which permits pressurization of the chamber with $CO_2$ gas;
   wherein when the $CO_2$ deliver device is in a second position the first opening is substantially aligned with the second port such that the second port and the chamber are in fluid communication and the first port is isolated between a third sealing member and a fourth sealing member such that the first port is not in fluid communication with the chamber, and wherein when a force is applied against the biasing member, the valve block is disposed into the second position which permits delivery of a bolus of pressurized $CO_2$ as from the chamber to a patient.

2. The $CO_2$ delivery device of claim 1, wherein the first position is independent from the second position.

3. The $CO_2$ delivery device of claim 1, wherein the syringe further comprises a threaded plunger, and wherein the syringe is configured to receive a threaded plunger.

4. The $CO_2$ delivery device of claim 1, further comprising:
   a $CO_2$ cartridge,
   wherein the $CO_2$ cartridge is directly coupled to the first port.

5. The $CO_2$ delivery device of claim 1, wherein each of the plurality of sealing members comprises an o-ring.

6. A $CO_2$ delivery device, comprising:
   a syringe, comprising
      a chamber; and
      a plunger; and
   a shuttle valve assembly, comprising
      a valve block having at least one opening;

a valve base having a first port and a second port;
a plurality of sealing members disposed between the valve block and the valve base; and
a biasing member biased against the valve block;
wherein when the $CO_2$ deliver device is in a first position the opening is substantially aligned with the first port such that the first port and the chamber are in fluid communication and the second port is isolated between a first sealing member and a second sealing member such that the second port is closed when the $CO_2$ delivery device is in a first position,
wherein when the $CO_2$ deliver device is in a second position the opening is substantially aligned with the second port such that the second port and the chamber are in fluid communication and the first port is isolated between a third sealing member and a fourth sealing member such that the first portion is closed when the $CO_2$ delivery device is in a second position, wherein the first position is independent from the second position, and wherein when a force is applied against the biasing member, the valve block is disposed into the second position which permits delivery of a bolus of pressurized $CO_2$ gas from the chamber to a patient.

7. The $CO_2$ delivery device of claim 6, wherein the biasing member is configured to maintain the $CO_2$ delivery device in the first position absent outside force from a practitioner.

8. The $CO_2$ delivery device of claim 7, wherein the $CO_2$ delivery device is disposed in the second position when a force is applied against the biasing member.

9. The $CO_2$ delivery device of claim 6, further comprising:
a pressure regulator; and
a $CO_2$ cartridge,
wherein the $CO_2$ cartridge is coupled to the pressure regulator, and
wherein the pressure regulator is coupled to the first port.

10. The $CO_2$ delivery device of claim 9, wherein the biasing member is configured to maintain the $CO_2$ delivery device in the first position such that the chamber is in fluid communication with the $CO_2$ cartridge.

11. The $CO_2$ delivery device of claim 10, wherein the $CO_2$ delivery device is disposed in the second position when a force is applied against the biasing member such that the chamber is in fluid communication with the second port for delivery of a bolus of $CO_2$ to a patient.

12. The $CO_2$ delivery device of claim 6, further comprising a $CO_2$ cartridge, wherein the $CO_2$ cartridge is coupled to the second port and the biasing member is configured to maintain the shuttle valve assembly in the first position, such that the chamber is in fluid communication with the first port, and wherein the $CO_2$ delivery device is disposed in the second position when a force is applied against the biasing member such that the chamber is in fluid communication with the $CO_2$ cartridge.

13. A system for introducing $CO_2$ as a contrast agent to a subject, the system comprising:
a $CO_2$ source; and
the $CO_2$ delivery device of claim 1,
wherein the $CO_2$ source is coupled to the $CO_2$ delivery device, and
wherein the $CO_2$ delivery device is configured to be coupled to the subject.

14. The system of claim 13, the system further comprising a pressure regulator.

15. The system of claim 14, the system further comprising a gas sensor.

16. The system of claim 15, the system further comprising a filter.

17. The system of claim 16, further comprising at least two tubing lines, wherein the $CO_2$ source is coupled to the $CO_2$ delivery device with at least one of the at least two tubing lines, and wherein the $CO_2$ delivery device is configured to be coupled to the subject with at least another of the at least two tubing lines.

18. A method for delivering $CO_2$ as a contrast agent to a subject, the method comprising:
coupling a $CO_2$ source at above atmospheric pressure to a $CO_2$ delivery device, wherein the $CO_2$ delivery device comprises:
a syringe; and
a shuttle valve assembly in fluid communication with a chamber of the syringe, the shuttle valve assembly comprising:
a valve block comprising an opening;
a valve base comprising a first port and a second port;
a plurality of sealing members disposed between the valve block and the valve base; and
a biasing member biased against the valve block,
wherein the $CO_2$ delivery device is in fluid communication with and receives pressurized $CO_2$ from the $CO_2$ source in a first position, wherein when the $CO_2$ delivery device is in the first position the opening of the valve block is substantially aligned with the first port of the valve base such that the first port and the chamber are in fluid communication and the second port of the valve base is isolated between a first sealing member and a second sealing member such that the second port is not in fluid communication with the chamber, and wherein the biasing member biases the valve block into the first position which permits pressurization of the chamber with $CO_2$ gas;
coupling the $CO_2$ delivery device to the subject;
actuating the $CO_2$ delivery device from the first position to a second position against the biasing force which delivers a bolus of $CO_2$ from the $CO_2$ delivery device to the subject, wherein when the $CO_2$ deliver device is in the second position the opening is substantially aligned with the second port of the valve base such that the second port and the chamber are in fluid communication and the first port is isolated between a third sealing member and a fourth sealing member such that the first port is not in fluid communication with the chamber; and
permitting the biasing force to automatically return the $CO_2$ delivery device back to the first position.

19. The method of claim 18, wherein the $CO_2$ delivery device is in fluid communication with the $CO_2$ source but not the subject when the $CO_2$ delivery device is engaged in the first position.

20. The method of claim 19, wherein the $CO_2$ delivery device is in fluid communication with the subject but not the $CO_2$ source when the $CO_2$ delivery device is engaged in the second position.

21. The method of claim 18, further comprising purging the $CO_2$ delivery device prior to coupling the $CO_2$ delivery device to the subject.

* * * * *

UNITED STATES PATENT AND TRADEMARK OFFICE
CERTIFICATE OF CORRECTION

PATENT NO. : 9,265,877 B2  
APPLICATION NO. : 13/756798  
DATED : February 23, 2016  
INVENTOR(S) : Gregory R. McArthur et al.

Page 1 of 1

It is certified that error appears in the above-identified patent and that said Letters Patent is hereby corrected as shown below:

In the Claims

Column 14, Line 31 reads, "... deliver device is in a ..." which should read "... delivery device is in a ..."

Column 14, Line 40 reads, "... deliver device is in a ..." which should read "... delivery device is in a ..."

Column 14, Line 49 reads, "... as from the chamber ..." which should read "... gas from the chamber ..."

Column 15, Line 5 reads, "... deliver device is in a ..." which should read "... delivery device is in a ..."

Column 15, Line 12 reads, "... deliver device is in a ..." which should read "... delivery device is in a ..."

Column 16, Line 42 reads, "... deliver device is in the ..." which should read "... delivery device is in the ..."

Signed and Sealed this  
Fifth Day of July, 2016

Michelle K. Lee  
*Director of the United States Patent and Trademark Office*